United States Patent
Achen et al.

(10) Patent No.: US 7,947,472 B2
(45) Date of Patent: *May 24, 2011

(54) EXPRESSION VECTORS AND CELL LINES EXPRESSING VASCULAR ENDOTHELIAL GROWTH FACTOR D

(75) Inventors: Marc G. Achen, Parkville (AU); Steven Alan Stacker, Parkville (AU); Kari Alitalo, Helsinki (FI)

(73) Assignee: Vegenics Limited, Toorak, Victoria (AU)

( * ) Notice: Subject to any disclaimer, the term of this patent is extended or adjusted under 35 U.S.C. 154(b) by 0 days.

This patent is subject to a terminal disclaimer.

(21) Appl. No.: 09/219,345

(22) Filed: Dec. 23, 1998

(65) Prior Publication Data

US 2002/0127222 A1    Sep. 12, 2002

Related U.S. Application Data

(60) Provisional application No. 60/087,392, filed on May 29, 1998.

(30) Foreign Application Priority Data

Dec. 24, 1997  (AU) ........................................ PP1131

(51) Int. Cl.
| | |
|---|---|
| C12N 5/071 | (2010.01) |
| C12N 5/00 | (2010.01) |
| C12N 15/09 | (2010.01) |
| C12N 15/12 | (2010.01) |
| C12N 15/63 | (2010.01) |
| C07H 21/04 | (2006.01) |

(52) U.S. Cl. ..................... 435/69.4; 435/320.1; 435/325; 435/366; 435/369; 536/23.5

(58) Field of Classification Search ................ 435/69.4, 435/70.1, 325, 366, 369, 320.1; 530/399
See application file for complete search history.

(56) References Cited

U.S. PATENT DOCUMENTS

| | | | | | |
|---|---|---|---|---|---|
| 4,851,341 | A | * | 7/1989 | Hopp et al. ................ | 435/69.7 |
| 5,179,007 | A | * | 1/1993 | Jarvis et al. ................ | 435/68.1 |
| 5,194,596 | A | * | 3/1993 | Tischer et al. | |
| 5,792,850 | A | * | 8/1998 | Baumgartner et al. ...... | 536/23.5 |
| 6,107,046 | A | | 8/2000 | Alitalo et al. | |
| 6,235,713 | B1 | | 5/2001 | Achen et al. | |
| 6,824,777 | B1 | | 11/2004 | Alitalo et al. | |
| 6,828,426 | B1 | * | 12/2004 | Hirata et al. ................ | 530/399 |
| 6,889,580 | B1 | | 5/2005 | Tseng | |
| 7,122,654 | B2 | | 10/2006 | Achen et al. | |

FOREIGN PATENT DOCUMENTS

| | | |
|---|---|---|
| EP | 0 935 001 | 8/1999 |
| WO | WO 95/24473 | 9/1995 |
| WO | WO 98/07832 | 2/1998 |
| WO | WO 98/24811 | 6/1998 |

OTHER PUBLICATIONS

Joukov et al. EMBO J. 15(2): 290-298, 1996.*
Yamada et al. Genomics 42: 483-488, 1997.*
Robson et al. Introduction to Proteins and Protein Engineering. Elsevier, New York, p. 41, 1986.*
Ngo et al. The Protein Folding Problem and Tertiary Structure Prediction. Birkhauser, Boston, pp. 492-495, 1994.*
Wells. Additivity of Mutational Effects in Proteins. Biochemistry 29(37): 8509-8517, 1990.*
Bowie et al. Deciphering the Message in Protein Sequences: Tolerance to Amino Acid Substitutions. Science 247: 1306-1310, 1990.*
Zrihan-Licht et al. J. Biol. Chem. 272(3): 1856-1863, 1997.*
Maurizio Orlandini, et al, Identification of a c-fos-Induced Gene that is related to the Platelet-derived Growth Factor/vascular Endothelial Growth Factor Family, Oct. 1996, Nat'l Acad. Sci. USA, vol. 93, pp. 11675-11680.
Yoshiki Yamada, et al, Molecular Cloning of a Novel Vascular Endothelial Growth Factor, VEGF-D, Apr. 1997, Genomics 42, pp. 483-488.
Notice to Declare Interference dated Aug. 26, 2009, Interference No. 105,695, Achen (U.S. Appl. No. 11/304,585) and Hirata (U.S. Appl. No. 11/397,289).
Interference Initial Memorandum, Interference No. 105,695 dated May 21, 2009, Achen (U.S. Appl. No. 11/304,585) and Hirata (U.S. Appl. No. 11/397,289).
Abandonment of Contest by Junior Party Achen et al., Interference No. 105,695 dated Jan. 5, 2010, Achen (U.S. Appl. No. 11/304,585) and Hirata (U.S. Appl. No. 11/397,289).
Response to Judgment—Request for Adverse, Interference No. 105,695 dated Jan. 6, 2010, Achen (U.S. Appl. No. 11/304,585) and Hirata (U.S. Appl. No. 11/397,289).
Notice to Declare Interference dated Apr. 3, 2003, Interference No. 105,098, Achen (U.S. Patent No. 6,235,713) and Hirata (U.S. Appl. No. 09/214,892).
Request for Adverse Judgment dated Oct. 13, 2003, Interference No. 105,098, Achen (U.S. Patent No. 6,235,713) and Hirata (U.S. Appl. No. 09/214,892).

* cited by examiner

*Primary Examiner* — Christine J Saoud
(74) *Attorney, Agent, or Firm* — Marshall, Gerstein & Borun LLP

(57) ABSTRACT

This invention relates to expression vectors comprising VEGF-D and its biologically active derivatives, cell lines stably expressing VEGF-D and its biologically active derivatives, and to a method of making a polypeptide using these expression vectors and host cells. The invention also relates to a method for treating and alleviating melanomas or tumors expressing VEGF-D and various diseases.

8 Claims, 11 Drawing Sheets

FIG. 4

```
GGAGAATGCC TTTTGCAACA CTTTTCAGTA GCTGCCTGGA AACAACTGCT
TAGTCATCGG TAGACATTTA AAATATTCAA AATGTATGGA GAATGGGGAA
TGGGGAATAT CCTCATGATG TTCCATGTGT ACTTGGTGCA GGGCTTCAGG
AGCGAACATG GACCAGTGAA GGATTTTCT TTTGAGCGAT CATCCCGGTC
CATGTTGGAA CGATCTGAAC AACAGATCCG AGCAGCTTCT AGTTTGGAGG
AGTTGCTGCA AATCGCGCAC TCTGAGGACT GGAAGCTGTG GCGATGCCGG
TTGAAGCTCA AAAGTCTTGC CAGTATGGAC TCACGCTCAG CATCCCATCG
CTCCACCAGA TTTGCGGCAA CTTTCTATGA CACTGAAACA CTAAAAGTTA
TAGATGAAGA ATGGCAGAGG ACCCAATGCA GCCCTAGAGA GACATGCGTA
GAAGTCGCCA GTGAGCTGGG GAAGACAACC AACACATTCT TCAAGCCCCC
CTGTGTAAAT GTCTTCCGGT GTGGAGGCTG CTGCAACGAA GAGGGTGTGA
TGTGTATGAA CACAAGCACC TCCTACATCT CCAAACAGCT CTTTGAGATA
TCAGTGCCTC TGACATCAGT GCCCGAGTTA GTGCCTGTTA AAATTGCCAA
CCATACGGGT TGTAAGTGCT TGCCCACGGG CCCCGCCAT CCTTACTCAA
TTATCAGAAG ATCCATTCAG ACCCCAGAAG AAGATGAATG TCCTCATTCC
AAGAAACTCT GTCCTATTGA CATGCTGTGG GATAACACCA AATGTAAATG
TGTTTTGCAA GACGAGACTC CACTGCCTGG GACAGAAGAC CACTCTTACC
TCCAGGAACC CACTCTCTGT GGACCGCACA TGACGTTTGA TGAAGATCGC
TGTGAGTGCG TCTGTAAAGC ACCATGTCCG GGAGATCTCA TTCAGCACCC
GGAAAACTGC AGTTGCTTTG AGTGCAAAGA AAGTCTGGAG AGCTGCTGCC
AAAAGCACAA GATTTTTCAC CCAGACACCT GCAGCTGTGA GGACAGATGT
CCTTTTCACA CCAGAACATG TGCAAGTAGA AAGCCAGCCT GTGGAAAGCA
CTGGCGCTTT CCAAAGGAGA CAAGGGCCCA GGACTCTAC AGCCAGGAGA
ACCCTTGATT CAACTTCCTT TCAAGTCCCC CCATCTCTGT CATTTTAAAC
AGCTCACTGC TTTGTCAAGT TGCTGTCACT GTTGCCCACT ACCCCTTGAA
CATGTGCAAA CACAGACACA CACACACACA CACACACAGA GCAACTAGGA
TTATGTTTTC TAGGTGCTGC CTAAG
```

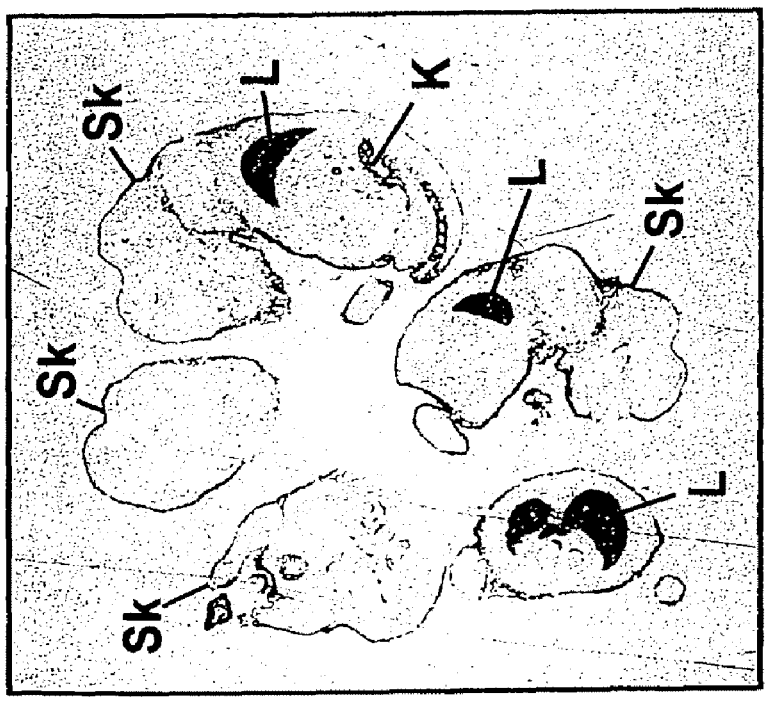
Figure 5B
Figure 5A

EXPRESSION VECTORS AND CELL LINES EXPRESSING VASCULAR ENDOTHELIAL GROWTH FACTOR D

This application claims the benefit of prior filed, provisional application No. 60/087,392, filed May 29, 1998.

BACKGROUND OF THE INVENTION

This invention relates to expression vectors comprising VEGF-D and its biologically active derivatives, cell lines stably expressing VEGF-D and its biologically active derivatives, and to a method of making a polypeptide using these expression vectors and host cells. The invention also relates to a method for treating and alleviating melanomas and various diseases.

Angiogenesis is a fundamental process required for normal growth and development of tissues, and involves the proliferation of new capillaries from pre-existing blood vessels. Angiogenesis is not only involved in embryonic development and normal tissue growth, repair, and regeneration, but is also involved in the female reproductive cycle, establishment and maintenance of pregnancy, and in repair of wounds and fractures. In addition to angiogenesis which takes place in the normal individual, angiogenic events are involved in a number of pathological processes, notably tumor growth and metastasis, and other conditions in which blood vessel proliferation, especially of the microvascular system, is increased, such as diabetic retinopathy, psoriasis and arthropathies. Inhibition of angiogenesis is useful in preventing or alleviating these pathological processes.

On the other hand, promotion of angiogenesis is desirable in situations where vascularization is to be established or extended, for example after tissue or organ transplantation, or to stimulate establishment of collateral circulation in tissue infarction or arterial stenosis, such as in coronary heart disease and thromboangitis obliterans.

Because of the crucial role of angiogenesis in so many physiological and pathological processes, factors involved in the control of angiogenesis have been intensively investigated. A number of growth factors have been shown to be involved in the regulation of angiogenesis; these include fibroblast growth factors (FGFs), platelet-derived growth factor (PDGF), transforming growth factor alpha (TGFα), and hepatocyte growth factor (HGF). See, for example, Folkman et al., J. Biol. Chem., 1992 267 10931-10934 for a review.

It has been suggested that a particular family of endothelial cell-specific growth factors and their corresponding receptors is primarily responsible for stimulation of endothelial cell growth and differentiation, and for certain functions of the differentiated cells. These factors are members of the PDGF family, and appear to act primarily via endothelial receptor tyrosine kinases (RTKs). Hitherto several vascular endothelial growth factor family members have been identified. Vascular endothelial growth factor (VEGF) is a homodimeric glycoprotein that has been isolated from several sources. VEGF shows highly specific mitogenic activity against endothelial cells, and can stimulate the whole sequence of events leading to angiogenesis. In addition, it has strong chemoattractant activity towards monocytes, can induce the plasminogen activator and the plasminogen activator inhibitor in endothelial cells, and can also influence microvascular permeability. Because of the latter activity, it is also sometimes referred to as vascular permeability factor (VPF). The isolation and properties of VEGF have been reviewed; see Ferrara et al., J. Cellular Biochem., 1991 47 211-218 and Connolly, J. Cellular Biochem., 1991 47 219-223.

More recently, six further members of the VEGF family have been identified. These are designated VEGF-B, described in International Patent Application PCT/US96/02957 (WO 96/26736) and in U.S. Pat. Nos. 5,840,693 and 5,607,918 by Ludwig Institute for Cancer Research and The University of Helsinki; VEGF-C, described in Joukov et al., The EMBO Journal, 1996 15 290-298; VEGF-D, described in International Patent Application No. PCT/US97/14696 (WO 98/07832); the placenta growth factor (PlGF), described in Maglione et al., Proc. Natl. Acad. Sci. USA, 1991 88 9267-9271; VEGF2, described in International Patent Application No. PCT/US94/05291 (WO 95/24473) by Human Genome Sciences, Inc; and VEGF3, described in International Patent Application No. PCT/US95/07283 (WO 96/39421) by Human Genome Sciences, Inc. Each show between 30% and 45% amino acid sequence identity with VEGF. The VEGF family members share a VEGF homology domain which contains the six cysteine residues which form the cysteine knot motif. Functional characteristics of the VEGF family include varying degrees of mitogenicity for endothelial cells, induction of vascular permeability and angiogenic and lymphangiogenic properties.

VEGF-B has similar angiogenic and other properties to those of VEGF, but is distributed and expressed in tissues differently from VEGF. In particular, VEGF-B is very strongly expressed in heart, and only weakly in lung, whereas the reverse is the case for VEGF. This suggests that VEGF and VEGF-B, despite the fact that they are co-expressed in many tissues, may have functional differences.

VEGF-B was isolated using a yeast co-hybrid interaction trap screening technique by screening for screening for cellular proteins which might interact with cellular retinoic acid-binding protein type I (CRABP-I). Its isolation and characteristics are described in detail in PCT/US96/02597 and in Olofsson et al., Proc. Natl. Acad. Sci. USA, 1996 93 2576-2581.

VEGF-C was isolated from conditioned media of PC-3 prostate adenocarcinoma cell line (CRL1435) by screening for ability of the medium to produce tyrosine phosphorylation of the endothelial cell-specific receptor tyrosine kinase VEGFR-3 (Flt4), using cells transfected to express VEGFR-3. VEGF-C was purified using affinity chromatography with recombinant VEGFR-3, and was cloned from a PC-3 cDNA library. Its isolation and characteristics are described in detail in Joukov et al., The EMBO Journal, 1996 15 290-298.

VEGF-D was isolated from a human breast cDNA library, commercially available from Clontech, by screening with an expressed sequence tag obtained from a human cDNA library designated "Soares Breast 3NbHBst" as a hybridization probe (Achen et al., Proc. Natl. Acad. Sci. USA, 1998 95 548-553). Its isolation and characteristics are described in detail in International Patent Application No. PCT/US97/14696.

In PCT/US97/14696, the isolation of a biologically active fragment of VEGF-D, designated VEGF-DΔNΔC, is also described. This fragment consists of VEGF-D amino acid residues 93 to 201 of SEQ ID NO: 11 (which corresponds to SEQ ID NO: 5 of PCT/US97/14696) linked to the affinity tag peptide FLAG®. The entire disclosure of the International Patent Application PCT/US97/14696 (WO 98/07832) is incorporated herein by reference.

VEGF-D has structural similarities to other members of the VEGF family. However, despite these structural similarities, it is structurally and functionally distinguished from other members of VEGF family. Human VEGF-D is only 48% identical to VEGF-C, which is the member of the family to which VEGF-D is most closely related.

The VEGF-D gene is broadly expressed in the adult human, but is certainly not ubiquitously expressed. VEGF-D is strongly expressed in heart, lung and skeletal muscle. Intermediate levels of VEGF-D are expressed in spleen, ovary, small intestine and colon, and a lower expression occurs in kidney, pancreas, thymus, prostate and testis. No VEGF-D mRNA was detected in RNA from brain, placenta, liver or peripheral blood leukocytes.

PlGF was isolated from a term placenta cDNA library. Its isolation and characteristics are described in detail in Maglione et al., Proc. Natl. Acad. Sci. USA, 1991 88 9267-9271. Presently its biological function is not well understood.

VEGF2 was isolated from a highly tumorgenic, oestrogen-independent human breast cancer cell line. While this molecule is stated to have about 22% homology to PDGF and 30% homology to VEGF, the method of isolation of the gene encoding VEGF2 is unclear, and no characterization of the biological activity is disclosed.

VEGF3 was isolated from a cDNA library derived from colon tissue. VEGF3 is stated to have about 36% identity and 66% similarity to VEGF. The method of isolation of the gene encoding VEGF3 is unclear and no characterization of the biological activity is disclosed.

Vascular endothelial growth factors appear to act primarily by binding to receptor tyrosine kinases. Five endothelial cell-specific receptor tyrosine kinases have been identified, namely VEGFR-1 (Flt-1), VEGFR-2 (KDR/Flk-1), VEGFR-3 (Flt4), Tie and Tek/Tie-2. All of these have the intrinsic tyrosine kinase activity which is necessary for signal transduction. The essential, specific role in vasculogenesis and angiogenesis of VEGFR-1, VEGFR-2, VEGFR-3, Tie and Tek/Tie-2 has been demonstrated by targeted mutations inactivating these receptors in mouse embryos.

The only receptor tyrosine kinases known to bind VEGFs are VEGFR-1, VEGFR-2 and VEGFR-3. VEGFR-1 and VEGFR-2 bind VEGF with high affinity, and VEGFR-1 also binds VEGF-B. VEGF-C has been shown to be the ligand for VEGFR-3, and also activates VEGFR-2 (Joukov et al., The EMBO Journal, 1996 15 290-298). VEGF-D shares receptor specificity with VEGF-C (Achen et al., Proc. Natl. Acad. Sci. USA, 1998 95 548-553). A ligand for Tek/Tie-2 has been described (International Patent Application PCT/US95/12935 (WO 96/11269) by Regeneron Pharmaceuticals, Inc.); however, the ligand for Tie has not yet been identified.

The primary translation products of VEGF-D and VEGF-C have long -and C-terminal polypeptide extensions in addition to a central VEGF homology domain (VHD). In the case of VEGF-C, these polypeptide extensions are propeptides which are proteolytically cleaved to generate a secreted form which consists only of the VHD and is capable of binding to VEGFR-2 and VEGFR-3 (Joukov et al., The EMBO Journal, 1996 15 290-298; Joukov et al., EMBO J., 1997 16 3898-3911). Likewise, a recombinant form of VEGF-D, consisting only of the VHD, was shown to bind and activate these receptors and to be mitogenic for endothelial cells, although VEGF-D processing was uncharacterized (Achen et al., Proc. Natl. Acad. Sci. USA, 1998 95 548-553).

Recently, a novel 130-135 kDa VEGF-A isoform specific receptor has been purified and cloned (Soker et al., Cell, 1998 92 735-745). The VEGF receptor was found to bind specifically the VEGF-$A_{165}$ isoform via the exon 7 encoded sequence, which shows weak affinity for heparin (Soker et al., Cell, 1998 92 735-745). Surprisingly, the receptor was shown to be identical to human neuropilin-1 (NP-1), a receptor involved in early stage neuromorphogenesis. PlGF-2 also appears to interact with NP-1 (Migdal et al., J. Biol. Chem., 1998 273 22272-22278).

Gene targeting studies have demonstrated the absolute requirement of VEGFR-1, VEGFR-2 and VEGFR-3 for embryonic development. These studies show that VEGFR-1 plays a role in vascular endothelial tube formation, VEGFR-2 is important for endothelial/hematopoietic cell differentiation and mitogenesis, and VEGFR-3 is involved in regulation of vascular remodeling, the formation of large vessels and in lymphangiogenesis. The functions of these receptors are reviewed in Mustonen and Alitalo, J. Cell Biol., 1995 129 895-898.

The VEGFR-3 is expressed in venous and lymphatic endothelia in the fetus, and predominantly in lymphatic endothelia in the adult (Kaipainen et al., Cancer Res, 1994 54 6571-6577; Proc. Natl. Acad. Sci. USA, 1995 92 3566-3570). VEGFR-3 has an essential role in the development of the embryonic cardiovascular system before the emergence of the lymphatic vessels (Dumont et al., Science, 1998 282 946-949). It has been suggested that VEGF-C may have a primary function in lymphatic endothelium, and a secondary function in angiogenesis and permeability regulation which is shared with VEGF (Joukov et al., The EMBO Journal, 1996 290-298).

SUMMARY OF THE INVENTION

The invention generally provides expression vectors comprising VEGF-D and its biologically active derivatives, cell lines stably expressing VEGF-D and its biologically active derivatives, and a method of making a polypeptide using these expression vectors and host cells. The invention also generally provides for a method for treating and alleviating melanomas or tumors expressing VEGF-D and various diseases.

According to a first aspect, the present invention provides a mammalian cell line stably expressing VEGF-D or a fragment or analog thereof having the biological activity of VEGF-D. Optionally VEGF-D produced by the cell line of the invention is linked to an epitope tag such as FLAG® (SEQ ID NO: 16), hexahistidine or I-SPY™ to assist in affinity purification and in localization of VEGF-D. Preferably the mammalian cell line is the 293-EBNA human embryonal kidney cell line. Preferably the VEGF-D expressed is VEGF-DFullNFlag, VEGF-DFulCFlag, VEGF-DΔNΔC, or VEGF-DΔC, as described herein.

The expression "biological activity of VEGF-D" is to be understood to mean the ability to stimulate one or more of endothelial cell proliferation, differentiation, migration, survival or vascular permeability.

A preferred fragment of VEGF-D is the portion of VEGF-D from amino acid residue 93 to amino acid residue 201 (i.e. the VEGF homology domain (VHD)) (SEQ ID NO:1) of SEQ ID NO: 11 (which corresponds to SEQ ID NO: 5 of PCT/US97/146961 optionally linked to the FLAG® peptide. Where the fragment is linked to FLAG®, the fragment is referred to herein as VEGF-DΔNΔC.

As used herein, the term "VEGF-D" collectively refers to any of the polypeptides of SEQ ID NOs: 11, 12, 13 and 14 (which correspond to SEQ ID NOs: 5, 3, 8 and 9, respectively, as defined in International Patent Application PCT/US97/14696), and SEQ ID NO: 15, which corresponds to amino acid residues 93 to 201 of SEQ ID NO: 14, and fragments or analogs thereof which have the biological activity of VEGF-D as herein defined.

According to a second aspect, the invention provides an expression vector comprising a sequence of human cDNA encoding VEGF-D, inserted into the mammalian expression vector Apex-3. Preferably the expression vector is pVDApex- FullNFlag, VEGF-DFullCFlag, pVDApexΔNΔC or pVDApexΔC, as described herein.

Preferably the expression vector also comprises a sequence encoding an affinity tag such as FLAG®, hexahistidine or I-SPY™.

The invention further provides a method of making a polypeptide according to the invention, comprising the steps of expressing an expression vector of the invention in a host cell, and isolating the polypeptide from the host cell or from the host cell's growth medium. In one preferred embodiment of this aspect of the invention, the expression vector further comprises a sequence encoding an affinity tag, such as FLAG®, hexahistidine or I-SPY™, in order to facilitate purification of the polypeptide by affinity chromatography.

The polypeptides comprising conservative substitutions, insertions or deletions but which still retain the biological activity of VEGF-D are clearly to be understood to be within the scope of the invention. Persons skilled in the art will be well aware of the methods which can be readily used to generate such polypeptides, for example the use of site-directed mutagenesis, or specific enzymatic cleavage and ligation. The skilled person will also be aware that peptidomimetic compounds or compounds in which one or more amino acid residues are replaced by a non-naturally occurring amino acid or an amino acid analog may retain the required aspects of the biological activity of VEGF-D. Such compounds can be readily made and tested by methods known in the art, and are also within the scope of the invention.

In addition, variant forms of the VEGF-D polypeptide which result from alternative splicing, as are known to occur with VEGF and VEGF-B, and naturally-occurring allelic variants of the nucleic acid sequence encoding VEGF-D are encompassed within the scope of the invention. Allelic variants are well known in the art, and represent alternative forms of the encoded polypeptide.

Such variant forms of VEGF-D can be prepared by targeting non-essential regions of the VEGF-D polypeptide for modification. These non-essential regions are expected to fall outside the strongly-conserved regions. In particular, the growth factors of the PDGF family, including VEGF, are dimeric, and VEGF, VEGF-B, VEGF-C, VEGF-D, PDGF-A and PDGF-B show complete conservation of eight cysteine residues in the PDGF-like domains (Olofsson et al., Proc. Natl. Acad. Sci. USA, 1996 93 2576-2581; Joukov et al., The EMBO Journal, 1996 15 290-298). These cysteines are thought to be involved in intra- and inter-molecular disulfide bonding. Loops 1, 2 and 3 of each subunit, which are formed by intra-molecular disulfide bonding, are involved in binding to the receptors for the PDGF/VEGF family of growth factors (Andersson et al., Growth Factors, 1995 12 159-164). As noted above, the cysteines conserved in previously known members of the VEGF family are also conserved in VEGF-D.

Persons skilled in the art thus are well aware that these cysteine residues should be preserved in any proposed variant form, and that the active sites present in loops 1, 2 and 3 also should be preserved. However, other regions of the molecule can be expected to be of lesser importance for biological function, and therefore offer suitable targets for modification. Modified polypeptides can be readily tested for their ability to show the biological activity of VEGF-D by routine activity assay procedures such as cell proliferation tests.

It is contemplated that some modified VEGF-D polypeptides will have the ability to bind to endothelial cells, i.e. to VEGF-D receptors, but which will be unable to stimulate endothelial cell proliferation, differentiation, migration or survival, or induce vascular permeability. These modified polypeptides are expected to be able to act as competitive or non-competitive inhibitors of VEGF-D, and to be useful in situations where prevention or reduction of VEGF-D action is desirable. Thus such receptor-binding but non-mitogenic, non-differentiation inducing, non-migration inducing or non-survival promoting variants of VEGF-D are also within the scope of the invention, and are referred to herein as "receptor-binding but otherwise inactive or interfering variants".

Likewise, it is contemplated that some modified VEGF-D polypeptides will have the ability to bind VEGF-D and will prevent binding of the dimer to VEGF-D receptors (e.g. VEGFR-2 and VEGFR-3) on endothelial cells. Thus these diners will be unable to stimulate endothelial cell proliferation, differentiation, migration or survival, or induce vascular permeability. These modified polypeptides are expected to be able to act as competitive or non-competitive inhibitors of VEGF-D, and to be useful in situations where prevention or reduction of VEGF-D action is desirable. Thus such VEGF-D-binding but non-mitogenic, non-differentiation inducing, non-migration inducing or non-survival promoting variants of VEGF-D are also within the scope of the invention, and are referred to herein as "VEGF-D-binding but otherwise inactive or interfering variants".

According to a third aspect, the invention provides a method of treatment or alleviation of malignant melanoma or tumors expressing VEGF-D, comprising the step of inhibiting the expression or activity of VEGF-D in the vicinity of the melanoma or tumor. Local inhibition of VEGF-D expression may be achieved for example by the use of anti-sense nucleic acid or triple-stranded DNA encoding VEGF-D. Alternatively a VEGF-D variant polypeptide, as described above, which has the ability to bind to VEGF-D and prevent binding to the VEGF-D receptors or which bind to the VEGF-D receptors, but which is unable to stimulate endothelial cell proliferation, differentiation, migration or survival may be used as a competitive or non-competitive inhibitor of VEGF-D. Small molecule inhibitors to VEGF-D, VEGFR-2 or VEGFR-3 and antibodies directed against VEGF-D, VEGFR-2 or VEGFR-3 may also be used.

Use of the above method is also contemplated in non-malignant conditions, where there is increased or continuous expression of VEGF-D, such as in psoriasis. Based on the distribution of VEGF-D in the skin of the developing mouse embryo it is possible that VEGF-D plays a role in the initiation or continuation of high epidermal cell turnover dermatoses such as psoriasis, where vascular proliferation in the upper dermis is a consistent and prominent histopathological feature.

In an additional aspect of the invention, VEGF-D is conjugated to toxins or drugs which have endothelial cell inhibiting activity that would be targeted to proliferating vascular and lymphatic endothelial cells which express VEGF-D receptors, e.g. VEGFR-2 and VEGFR-3. Thus, growth of vessels, which is important for numerous pathological conditions, such as tumor growth, could be blocked.

According to a fifth aspect, the invention provides a method of enhancing the acceptance and/or healing of a skin graft, comprising the step of stimulating angiogenesis and lymphangiogenesis with an effective dose of VEGF-D, or a fragment or analog thereof having the biological activity of VEGF-D.

According to a sixth aspect, the invention provides a method of stimulating the healing of a surgical or traumatic wound to the skin, comprising the step of stimulating angiogenesis and lymphangiogenesis with an effective dose of VEGF-D, or a fragment or analog thereof having the biological activity of VEGF-D.

It is contemplated that the latter two aspects of the invention will be particularly useful in the treatment of burns and in plastic surgery.

In another aspect of the invention a method is provided for stimulating lymphangiogenesis for treatment or alleviation of lymphedema, comprising the step of stimulating lymphangiogenesis with an effective dose of VEGF-D, or a fragment or analog thereof having the biological activity of VEGF-D. Few diseases are as disfiguring as lymphedema. Lymphedema occurs when there is obstruction of the lymphatic vessels which are involved in the draining of fluid bathing the tissues. As a result of this obstruction, lymph or fatty fluid accumulates within the tissues and results in limb and tissue engorgement. The end result is often grotesque and severely incapacitating due to local infections, discomfort and deformity. There are several causes of lymphedema. Most notable is breast cancer associated with either lymph node obstruction or removal during surgery. Recurrent infections and other forms of surgery are also associated with lymphedema. A significant proportion of patients with lymphedema have no identifiable precitant. Increasing the amount of VEGF-D should induce lymphangiogenesis and alleviate lymph and fatty fluid accumulation.

Inappropriate down-regulation of VEGF-D synthesis during embryogenesis may also be important in adnexal structure maldevelopment including anhydrotic ectodermal dysplasia. Normally the sweat glands in the dermis are surrounded by vascularized fatty connective tissue. If the vascular supply is compromised or unable to replenish due to a possible lack of VEGF-D, it will lead to sweat gland hypoxia and malfunction. These lesions may be due to lack of ability of differentiated cells at some stage of development to produce VEGF-D or production of blocking agents to the VEGF-D receptors on blood vessels adjacent to differentiating adnexal cells producing such blocking agents. Thus the invention provides a method for treating or alleviating anhydrotic ectodermal dysplasia by stimulating vascularization of fatty connective tissue, comprising the step of administering an effective dose of VEGF-D, or a fragment or analog thereof having the biological activity of VEGF-D.

A further disease which may be related to a lack of VEGF-D or lack of response to VEGF-D is scleroderma. Scleroderma is an uncommon disorder of connective tissue characterized by thickening and increased collagenization of the skin that is thought to be due to changes in vascularization and/or fibroblast function. Damage to the endothelial cells due to a lack of VEGF-D or to a failure to response to VEGF-D may be a contributing factor to the inability of the vessels to repair leading to the continued platelet aggregation observed and subsequent release of growth factors having a mitogenic action on fibroblasts. This results in increased collagen production. The same considerations apply to systemic organ involvement in scleroderma. Thus the invention provides a method for treating or alleviating scleroderma by stimulating proliferation of vascular endothelial cells, comprising the step of administering an effective dose of VEGF-D, or a fragment or analog thereof having the biological activity of VEGF-D.

According to a seventh aspect, the invention provides a method for stimulating at least one bioactivity of VEGF-D selected from endothelial cell proliferation, migration, survival and differentiation, and lymphangiogenesis without inducing vascular permeability, comprising the step of administering a bioactivity stimulating amount of fully processed VEGF-D.

A further aspect of the invention provides a method for regulating receptor-binding specificity of VEGF-D, comprising the steps of expressing an expression vector comprising a nucleotide sequence encoding an unprocessed VEGF-D and supplying a proteolytic amount of at least one enzyme for processing the encoded VEGF-D to generate a proteolytically processed form of VEGF-D.

It will be clearly understood that for the purposes of this specification the phrase "fully processed VEGF-D" means a VEGF-D polypeptide without the N- and C-terminal propeptides, the phrase "proteolytically processed form of VEGF-D" means a VEGF-D polypeptide without the N- and/or C-terminal propeptide, and the phrase "unprocessed VEGF-D" means a VEGF-D polypeptide with both the N- and C-terminal propeptides.

The invention also provides a method of detecting tumors expressing VEGF-D in a biological sample, comprising the steps of contacting said sample with a specific binding reagent for VEGF-D, allowing time for a binding of said specific binding reagent to VEGF-D, and detecting said binding. In a preferred embodiment the specific binding reagent for VEGF-D is an antibody and the binding and/or extent of binding is detected by means of an antibody with a detectable label. Quantitation of VEGF-D in cancer biopsy specimens will be useful as an indicator of future metastatic risk.

Antibodies according to the invention may be labeled with a detectable label, and utilized for diagnostic purposes. The antibody may be covalently or non-covalently coupled to a suitable supermagnetic, paramagnetic, electron dense, ecogenic or radioactive agent for imaging. For use in diagnostic assays, radioactive or non-radioactive labels may be used. Examples of radioactive labels include a radioactive atom or group, such as $^{125}I$ or $^{32}P$. Examples of non-radioactive labels include enzyme labels, such as horseradish peroxidase, or fluorimetric labels, such as fluorescein-5-isothiocyanate (FITC). Labeling may be direct or indirect, covalent or non-covalent.

The polypeptides or antibodies which induce the biological activity of VEGF-D may be employed in combination with a suitable pharmaceutical carrier. The polypeptides, VEGF-D antagonists or antibodies which inhibit the biological activity of VEGF-D also may be employed in combination with a suitable pharmaceutical carrier. Such compositions comprise a therapeutically effective amount of the antibody, and a pharmaceutically acceptable carrier or adjuvant. Examples of such a carrier include, but are not limited to, saline, buffered saline, mineral oil, talc, dextrose, water, glycerol, ethanol, thickeners, stabilizers, suspending agents and combinations thereof. Such compositions may be in the form of solutions, suspensions, tablets, capsules, creams, salves, ointments or other conventional forms. The formulation is selected to suit the mode of administration. Where polypeptides, VEGF-D antagonists or antibodies are to be used for therapeutic purposes, the dose and route of application will depend upon the nature of the patient and condition to be treated, and will be at the discretion of the attending physician or veterinarian. Suitable routes include subcutaneous, intramuscular, intraperitoneal or intravenous injection, topical application, implants etc. Topical application of VEGF-D may be used in a manner analogous to VEGF.

It will be clearly understood that for the purposes of this specification the word "comprising" means "including but not limited to". The corresponding meaning applies to the word "comprises".

BRIEF DESCRIPTION OF THE DRAWINGS

FIG. 4 shows the nucleotide sequence of a cDNA encoding mouse VEGF-D1 (SEQ ID NO:2), isolated by hybridization screening from a commercially-available mouse lung cDNA library;

FIGS. 5A and 5B show autoradiographs taken after two days of exposure to mouse 15.5 days post-coital tissue sections hybridized with VEGF-D antisense (FIG. 5A) and sense (FIG. 5B) RNAs;

DETAILED DESCRIPTION OF PREFERRED EMBODIMENTS

Example 1

Cell Lines Stably Expressing VEGF-D Derivatives

Figure 1:
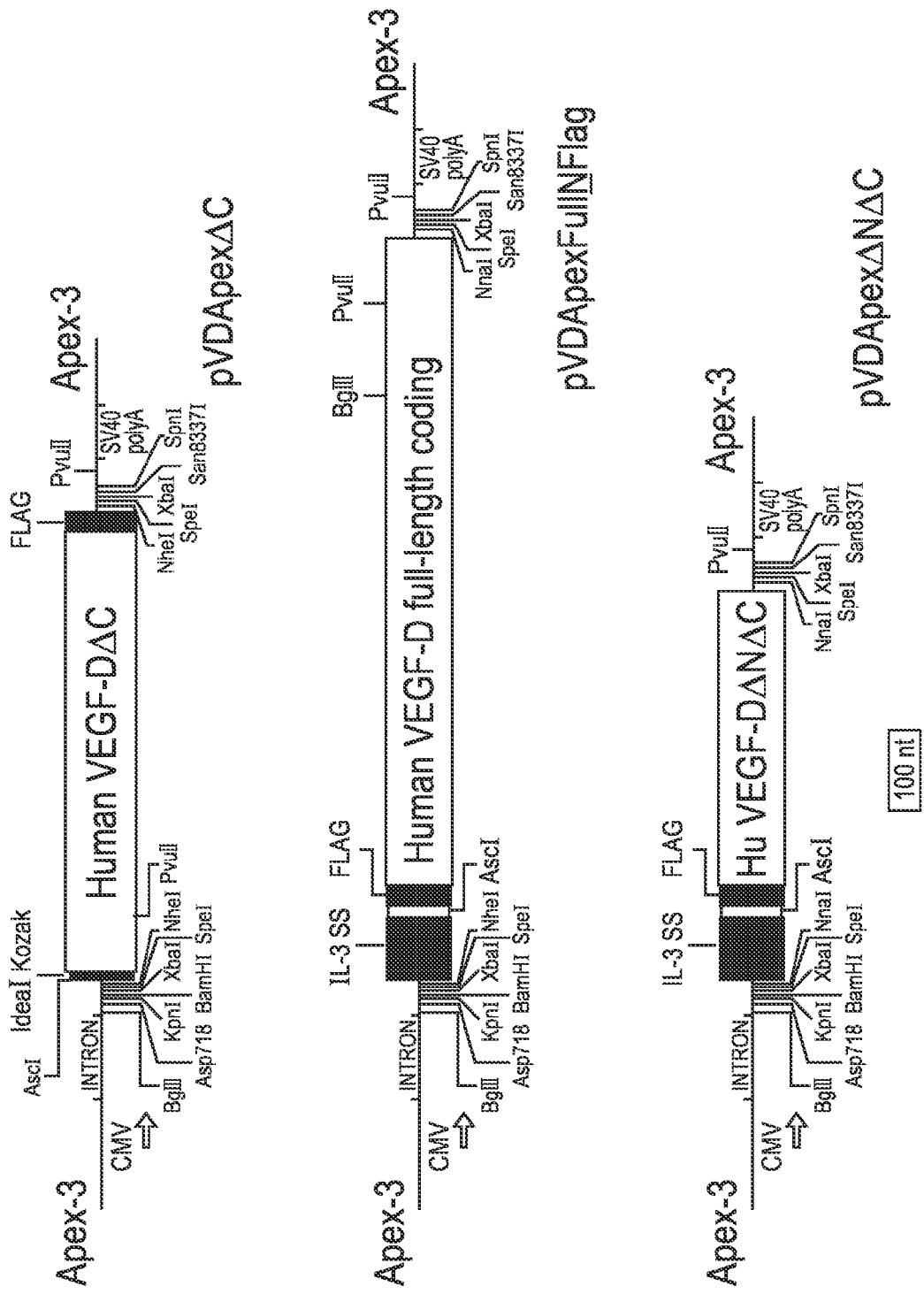
FIG. 1 shows schematic maps of the Apex-3 plasmid constructs for expression of human VEGF-D derivatives in 293-EBNA cells.

In order to generate cell lines constitutively expressing derivatives of VEGF-D, regions of the human VEGF-D cDNA were inserted into the mammalian expression vector Apex-3 (Evans et al, Mol. Immunol., 1995 32 1183-1195). This vector is maintained episomally when transfected into 293-EBNA human embryonal kidney cells. For expression of VEGF-DΔNΔC, A DNA fragment encoding residues 93 to 201 (SEQ ID NO:1) was amplified by polymerase chain reaction (PCR) with Pfu DNA polymerase, using as template a plasmid comprising full length VEGF-D cDNA (SEQ ID NO: 10). The amplified DNA fragment, the correctness of which was confirmed by nucleotide sequencing, was then inserted into the expression vector pEFBOSSFLAG (a gift from Dr. Clare McFarlane at the Walter and Eliza Hall Institute for Medical Research (WEHI), Melbourne, Australia, as described in Evans, et al., J. Immunol. Methods, 184:123-135 (1995)), to give rise to a plasmid designated pEFBOSVEGF-DΔNΔC. The pEFBOSVEGF-DΔNΔC vector contains DNA encoding the signal sequence for protein secretion from the interleukin-13 (IL-3) gene and the FLAG® octapeptide (Sigma Aldrich). The FLAG® octapeptide can be recognized by commercially available antibodies such as the M2 monoclonal antibody (Sigma Aldrich). The VEGF-D PCR fragment was inserted into the vector such that the IL-3 signal sequence was immediately upstream from the FLAG® octapeptide, which was in turn immediately upstream from the truncated VEGF-D sequence. All three sequences were in the same reading frame, so that translation of mRNA resulting from transfection of pEFBOSVEGF-DΔNΔC into mammalian cells would give rise to a protein which would have the IL-3 signal sequence at its N-terminus, followed by the FLAG® octapeptide and the truncated VEGF-D sequence. Cleavage of the signal sequence and subsequent secretion of the protein from the cell would give rise to a VEGF-D polypeptide which is tagged with the FLAG® octapeptide adjacent to the N-terminus. The region of pEFBOSVEGF-DΔNΔC containing the sequence encoding the IL-3 signal sequence, the FLAG® octapeptide and the DNA fragment encoding residues 93 to 201 of VEGF-D (SEQ ID NO:1) was inserted into the XbaI site of Apex-3. The resulting plasmid was designated pVDApexΔNΔC, and is illustrated schematically in FIG. 1.

In addition, a second plasmid was constructed, designated pEFBOSVEGFDfullFLAG, in which the full length coding sequence of human VEGF-D (SEQ ID NO: 10) was inserted into EFBOSIFLAG such that the sequence for the FLAG® octapeptide was immediately downstream from, and in the same reading frame as, the coding sequence of VEGF-D. The plasmid pEFBOSIFLAG lacks the IL-3 signal sequence, so secretion of the VEGF-D/FLAG fusion protein was driven by the signal sequence of VEGF-D. pEFBOSVEGFDfullFLAG was designed to drive expression in mammalian cells of full-length VEGF-D which was C-terminally tagged with the FLAG® octapeptide. This protein is designated VEGFD-fullCFLAG. The resulting plasmid was designated pVDApexΔNΔC, and is illustrated schematically in FIG. 1.

Similar types of constructs were made for expression of VEGF-DFullNFlag, a derivative of full-length human VEGF-D (SEQ ID NO: 11) which had been tagged with FLAG® at the N-terminus, and for expression of a truncated derivative of human VEGF-D, consisting of amino acid residues 2 to 202 (SEQ ID NO: 11), designated VEGF-DΔC. The expression constructs for these VEGF-D derivatives were designated pVDApexFullNFlag and pVDApexΔC respectively, and are also shown schematically in FIG. 1. IL-3 SS denotes the interleukin-3 signal sequence, and the arrows indicate the direction of transcription proceeding from the cytomegalovirus promoter (CMV) through the expression cassettes. These vectors were transfected into cells of the human embryo kidney cell line 293-EBNA by the calcium phosphate method, and stable transfectants were selected in the presence of hygromycin. Cell lines expressing high levels of VEGF-DFullNFlag, VEGF-DΔC and VEGF-DΔNΔC were subsequently identified by metabolic labeling, immunoprecipitation and Western blot analysis, as shown in FIG. 2.

Figure 2:
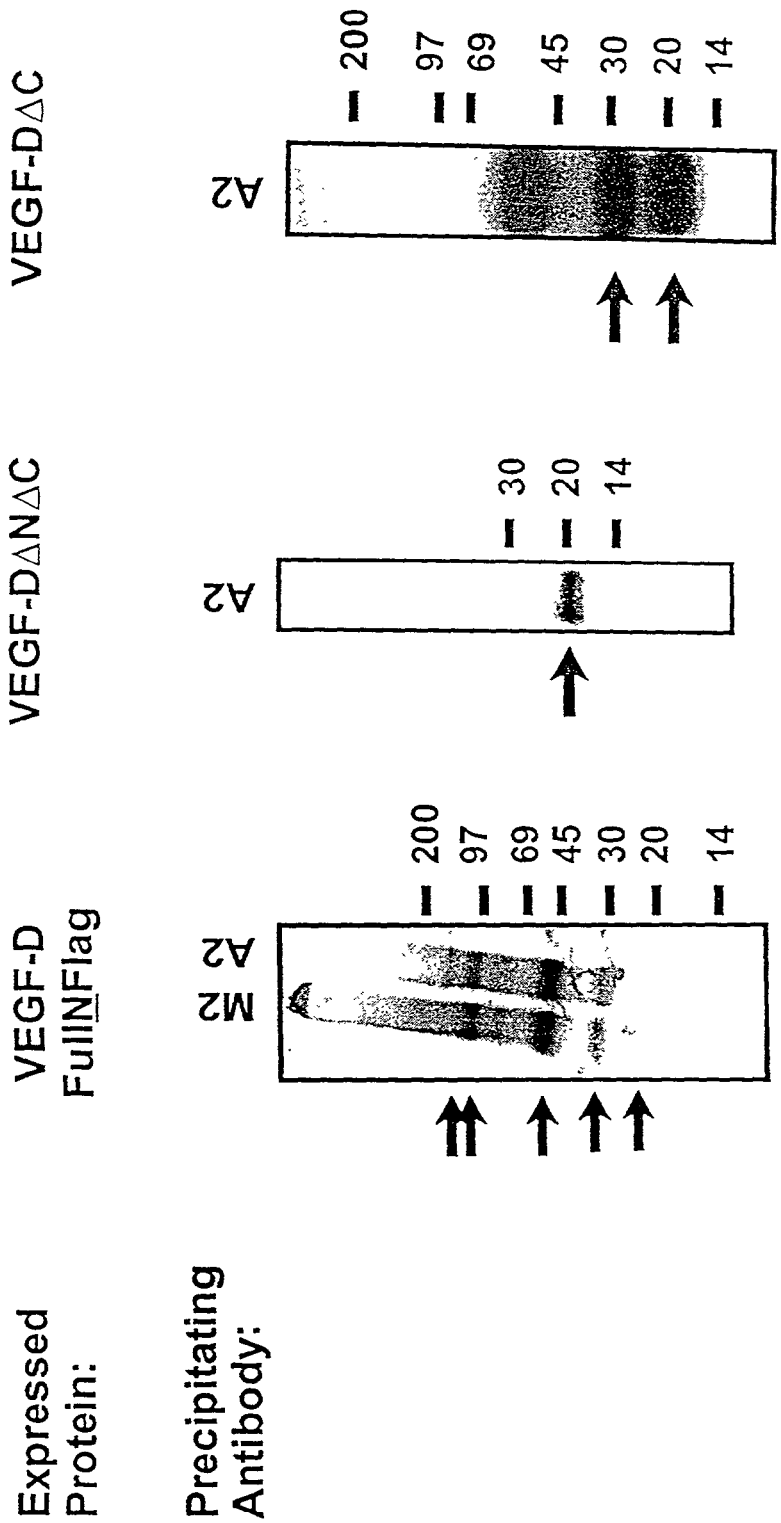
FIG. 2 shows the expression of VEGF-D derivatives by 293-EBNA cells.

In FIG. 2, the 293-EBNA cell lines expressing VEGF-DFullNFlag, VEGF-DΔNΔC and VEGF-DΔC were metabolically labeled, and proteins in conditioned medium samples were immunoprecipitated with anti-FLAG antibody (M2) or with antiserum specific for the VEGF homology domain of VEGF-D (A2). The precipitated proteins were analyzed by SDS-PAGE and visualized by autoradiography in the case of VEGF-DFullNFlag and VEGF-DΔNΔC or detected in Western blot analysis with M2 antibody in the case of VEGF-DΔC. Arrows denote the positions of VEGF-D derivatives. These derivatives were not detected from control supernatants derived from parental 293-EBNA cells (data not shown). The positions of molecular weight markers (in kDa), are shown to the right of each panel. The band at approximately 50 kDa detected by Western blot analysis of VEGF-DΔC corresponds to the immunoglobulin heavy chain.

Numerous VEGF-D derivatives were detected in the supernatants of cells expressing VEGF-DFullNFlag and VEGF-DΔC. These derivatives are formed as a result of proteolytic processing which occurs as part of the biosynthesis of VEGF-D. The cell lines expressing VEGF-DNFullFlag, VEGF-DΔC and VEGF-DΔNΔC have been maintained under hygromycin selection while being passaged at least twenty times, and continue to express the VEGF-D derivatives.

Example 2

Binding of VEGF-DΔNΔC to Soluble VEGF Receptors

To further assess the interactions between VEGF-D and the VEGF receptors, VEGF-DΔNΔC was tested for its capacity to bind to soluble immunoglobulin fusion proteins comprising the extracellular domains of human VEGFR-1, human VEGFR-2 and human VEGFR-3. The corresponding fragment of VEGF-C, VEGF-CΔNΔC, was used for comparison. For binding experiments, 293T human embryonal kidney cells were transfected with plasmids encoding the soluble receptor-immunoglobulin fusion proteins VEGFR-1-Ig, VEGFR-2-Ig or VEGFR-3-Ig using the calcium-phosphate (Ca-phosphate) method. In these fusion proteins, the extracellular domain of the relevant VEGF receptor is fused to the Fc portion of human IgG.sub.1. The cells were incubated for 24 hours after transfection, washed with Dulbecco's Modified Eagle's Medium (DMEM) containing 0.2% bovine serum albumin (BSA) and starved for 24 hours. Media were then collected and clarified by centrifugation, and fusion proteins were precipitated using protein A Sepharose beads. The Sepharose beads were then incubated at room temperature for 3 hours with 900 µl of metabolically .sup.35S-labeled medium from 293-EBNA cells which had been transfected with expression plasmids encoding human VEGF-DΔNΔC, human VEGF-CΔNΔC or human VEGF.sub.15 using the Ca-phosphate method. Metabolic labeling of 293-EBNA cells was carried out essentially as described (Joukov et al., 1997). The Sepharose beads were then washed twice with binding buffer (0.5% BSA, 0.02% Tween 20, 1 µg/ml heparin in phosphate buffered saline (PBS)) at 4.degree. C. and once with PBS, boiled in Laemmli sample buffer, and proteins were then analyzed by SDS-PAGE. The results are shown in FIG. 3.

Figure 3:
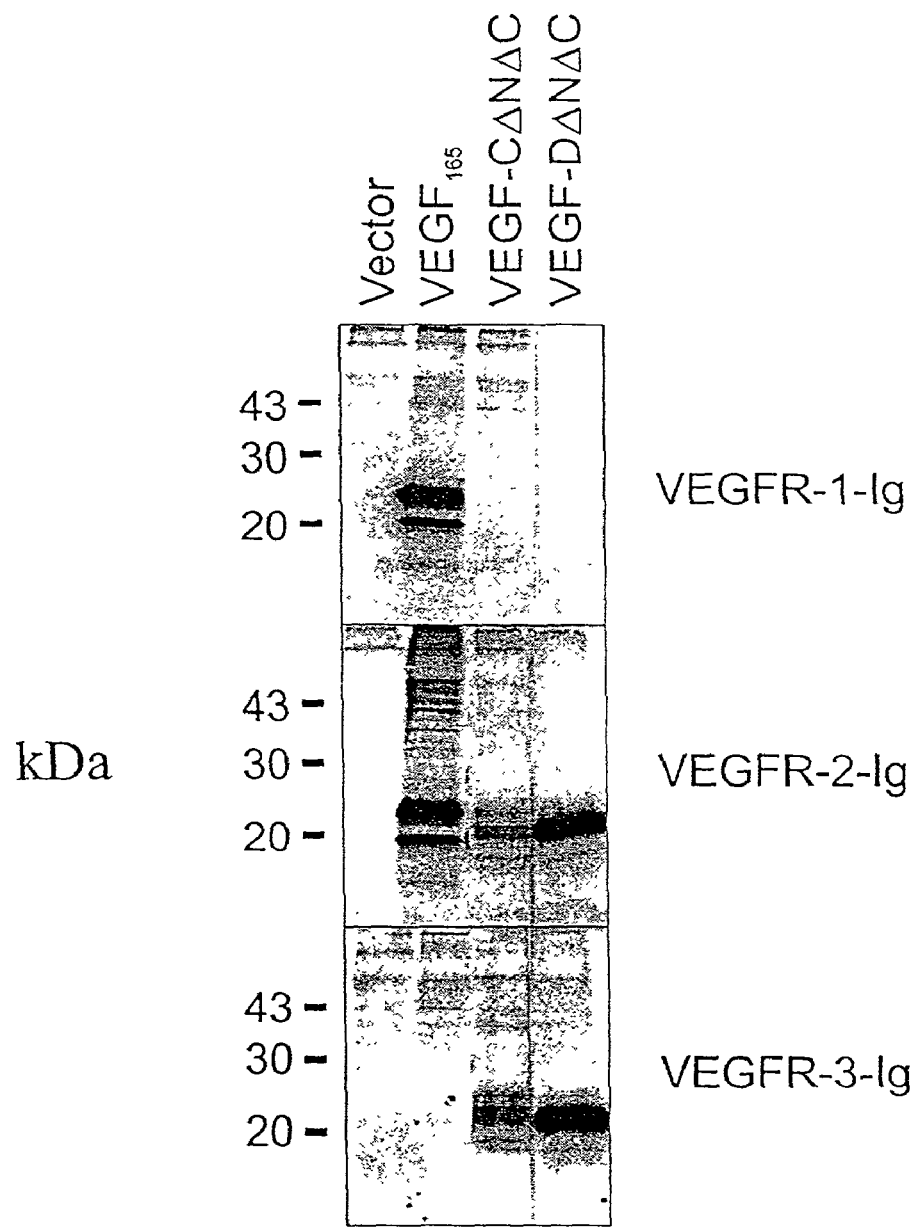
FIG. 3 shows the precipitation of VEGF-D by soluble VEGF receptor-immunoglobulin fusion proteins.

In FIG. 3, precipitation of labeled VEGF$_{165}$, VEGF-CΔNΔC and VEGF-DΔNΔC by VEGFR-1-Ig, VEGFR-2-Ig and VEGFR-3-Ig was carried out as described above. The fusion proteins used for the precipitations are shown to the right. "Vector" denotes results of precipitations from medium derived from cells transfected with expression vector lacking sequence encoding the VEGFs. The molecular weight markers are indicated in kDa A polypeptide of the size expected for VEGF-DΔNΔC (approximately 22 kDa) was precipitated by VEGFR-2-Ig and VEGFR-3-Ig from the medium of cells expressing VEGF-DΔNΔC. In contrast, no protein of this size was precipitated from the same medium by VEGFR-1-Ig. Essentially the same results were observed for precipitation of VEGF-CΔNΔC. As expected, a predominant polypeptide of approximately 24 kDa was precipitated by VEGFR-1-Ig and VEGFR-2-Ig from the medium of cells expressing VEGF$_{165}$, but was not precipitated by VEGFR-3-Ig. No labeled polypeptides were precipitated by the three fusion proteins from the medium of cells transfected with the expression vector lacking sequences encoding the VEGFs. These data indicate that VEGF-DΔNΔC can bind to VEGFR-2 and VEGFR-3 but not to VEGFR-1. Thus VEGF-DΔNΔC resembles VEGF-CΔNΔC in the receptor-binding specificity to VEGFR-2 and VEGFR-3.

Example 3

In Situ Hybridization Studies of VEGF-D Gene Expression in Mouse Embryos

The pattern of VEGF-D gene expression was studied by in situ hybridization using a radiolabeled antisense RNA probe corresponding to nucleotides 1 to 340 of the mouse VEGF-D1 cDNA, whose sequence is shown in FIG. 4. The antisense RNA was synthesized by in vitro transcription with T3 RNA polymerase and [$^{35}$S] UTPαs. Mouse VEGF-D is fully described in International Patent application PCT/US97/14696. This antisense RNA probe was hybridized to paraffin-embedded tissue sections of mouse embryos at post-coital day 15.5. The labeled sections were subjected to autoradiography for 2 days. The resulting autoradiographs for sections hybridized to the antisense RNA and to complementary sense RNA (as negative control) are shown in FIG. 5A-B. In FIG. 5A, "L" denotes lung and "Sk" denotes skin, and the two tissue sections shown are serial sections. Strong signals for VEGF-D mRNA were detected in the developing lung and associated with the skin. No signals were detected using the control sense RNA (FIG. 5B).

Figure 6A:
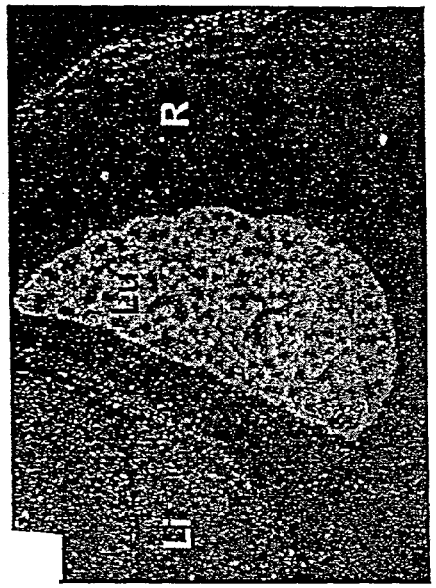
FIGS. 6A-6D show the results of analysis of the distribution of VEGF-D mRNA in the post-coital day 15.5 mouse embryo by in situ hybridization.
Figure 6B:
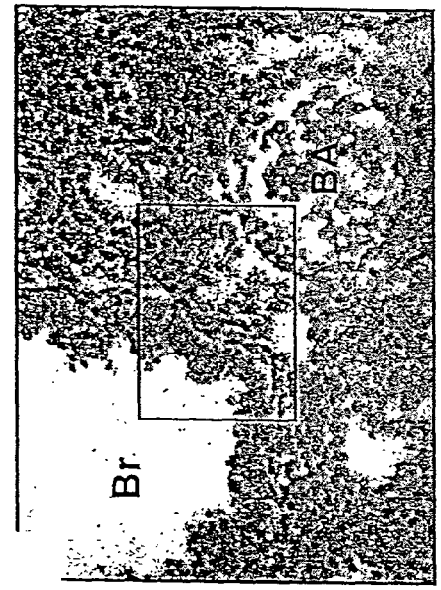
Figure 6C:
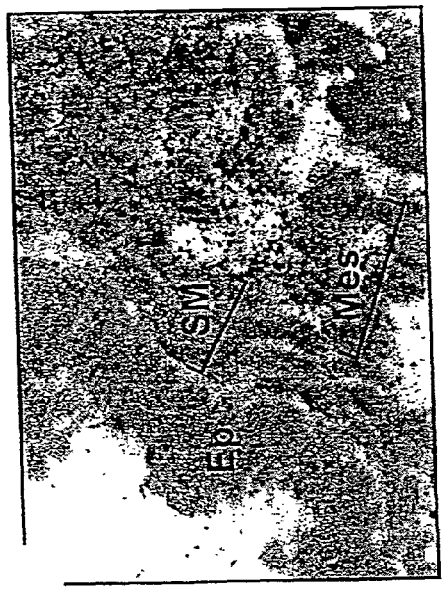
Figure 6D:
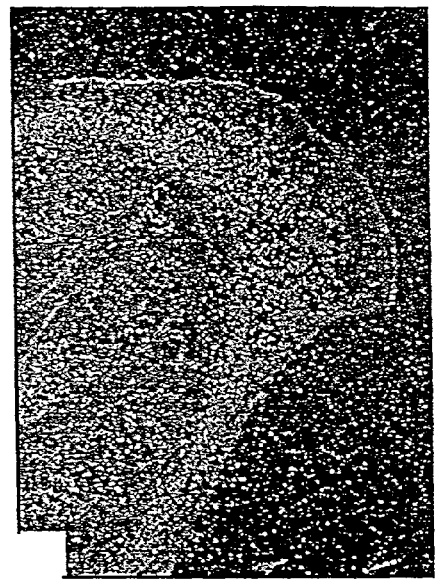

In FIGS. 6A-D, sagittal tissue sections were hybridized with VEGF-D antisense RNA probe and subsequently incubated with photographic emulsion, developed and stained. Microscopic analysis revealed that VEGF-D mRNA was abundant in the mesenchymal cells of the developing lung (FIG. 6A-C). In contrast, the epithelial cells of the bronchi and bronchioles were negative, as were the developing smooth muscle cells surrounding the bronchi. The endothelial cells of bronchial arteries were also negative. In FIG. 6A, the dark field micrograph shows a strong signal for VEGF-D mRNA in lung (Lu). Liver (Li) and ribs (R) are also shown. FIG. 6B shows a higher magnification of the lung. The light field micrograph shows a bronchus (Br) and bronchial artery (BA). The black outline of a rectangle denotes the region of the section shown in FIG. 6C but at a higher magnification. FIG. 6C shows the epithelial cells of the bronchus (Ep), the developing smooth muscle cells (SM) surrounding the epithelial cell layer and the mesenchymal cells (Mes). The abundance of silver grains associated with mesenchymal cells is apparent. In FIG. 6D, a dark field micrograph shows a limb bud. A strong signal was located immediately under the skin in a region of tissue rich in fibroblasts and developing melanocytes. The magnification for FIGS. 6A and D is ×40, for FIG. 6B, it is ×200 and for FIG. 6C, it is ×500.

The results presented here suggest that VEGF-D may attract the growth of blood and lymphatic vessels into the developing lung and into the region immediately underneath the skin. Due to the expression of the VEGF-D gene adjacent to the skin, it is considered that VEGF-D could play a role in inducing the angiogenesis that is associated with malignant melanoma. Malignant melanoma is a very highly vascularized tumor. This suggests that local inhibition of VEGF-D expression, for example using VEGF-D or VEGF receptor-2 or VEGF receptor-3 antibodies, is useful in the treatment of malignant melanoma. Other suitable inhibitors of VEGF-D activity, such as anti-sense nucleic acids or triple-stranded DNA, may also be used.

Example 4

Production of Monoclonal Antibodies that Bind to Human VEGF-D

Monoclonal antibodies to VEGF-DΔNΔC were raised in mice. VEGF-DΔNΔC includes the amino acid sequence of the VHD of VEGF-D and is similar in sequence to all other members of the VEGF family. Therefore, it is thought that the bioactive portion of VEGF-D likely resides in the VHD. A DNA fragment encoding a truncated portion of human VEGF-D from residue 93 to 201, i.e. with the N- and C-terminal regions removed, was amplified by polymerase chain reaction (PCR) with Pfu DNA polymerase, using as template a plasmid comprising full-length human VEGF-D cDNA. The amplified DNA fragment, the sequence of which was confirmed by nucleotide sequencing, was then inserted into the expression vector pEFBOSSFLAG (a gift from Dr. Clare McFarlane at the Walter and Eliza Hall Institute for Medical Research (WEHI), Melbourne, Australia) to give rise to a plasmid designated pEFBOSVEGF-DΔNΔC. The pEFBOSSFLAG vector contains DNA encoding the signal sequence for protein secretion from the interleukin-3 (IL-3) gene and the FLAG® octapeptide (Sigma-Aldrich). The FLAG® octapeptide can be recognized by commercially available antibodies such as the M2 monoclonal antibody (Sigma-Aldrich). The VEGF-D PCR fragment was inserted into the vector such that the IL-3 signal sequence was immediately upstream from the FLAG® octapeptide, which was in turn immediately upstream from the truncated VEGF-D sequence. All three sequences were in the same reading frame, so that translation of mRNA resulting from transfection of pEFBOSVEGF-DΔNΔC into mammalian cells would give rise to a protein which would have the IL-3 signal sequence at its N-terminus, followed by the FLAG® octapeptide and the truncated VEGF-D sequence. Cleavage of the signal sequence and subsequent secretion of the protein from the cell would give rise to a VEGF-D polypeptide which is tagged with the FLAG® octapeptide adjacent to the N-terminus. This protein was designated VEGF-DΔNΔC. VEGF-DΔNΔC was purified by anti-FLAG® affinity chromatography from the medium of COS cells which had been transiently transfected with the plasmid pEFBOSVEGF-DΔNΔC. (see Example 9 in International Patent Application No. PCT/US97/14696).

Purified VEGF-DΔNΔC was used to immunize female Balb/C mice on day 85 (intraperitoneal), 71 (intraperitoneal) and 4 (intravenous) prior to the harvesting of the spleen cells from the immunized mice and subsequent fusion of these spleen cells to mouse myeloma P3X63Ag8.653 (NS-1) cells. For the first two immunizations, approximately 10 µg of VEGF-DΔNΔC in a 1:1 mixture of PBS and TiterMax adjuvant (#R-1 Research adjuvant; CytRx Corp., Norcross, Ga.) were injected, whereas for the third immunization 35 µg of VEGF-DΔNΔC in PBS was used.

Monoclonal antibodies to VEGF-DΔNΔC were selected by screening the hybridomas on purified VEGF-DΔNΔC using an enzyme immunoassay. Briefly, 96-well microtiter plates were coated with VEGF-DΔNΔC, and hybridoma supernatants were added and incubated for 2 hours at 4° C., followed by six washes in PBS with 0.02% Tween 20. Incubation with a horse radish peroxidase conjugated anti-mouse Ig (Bio-Rad, Hercules, Calif.) followed for 1 hour at 4° C. After washing, the assay was developed with an 2,2'-azino-di-(3-ethylbenz-thiazoline sulfonic acid) (ABTS) substrate system (Zymed, San Francisco, Calif.), and the assay was quantified by reading absorbance at 405 nm in a multiwell plate reader (Flow Laboratories MCC/340, McLean, Va.) Six antibodies were selected for further analysis and were subcloned twice by limiting dilution. These antibodies were designated 2F8, 3C10, 4A5, 4E10, 4H4 and 5F12. The isotypes of the antibodies were determined using an Isostrip™ isotyping kit (Boehringer Mannheim, Indianapolis, Ind.) Antibodies 2F8, 4A5, 4E10 and 5F12 were of the IgG.sub.I class whereas 4H4 and 3C10 were of the IgM class. All six antibodies contained the kappa light chain.

Hybridoma cell lines were grown in DMEM containing 5% v/v IgG-depleted serum (Gibco BRL, Gaithersburg, Md.), 5 mM L-glutamine, 50 µg/ml gentamicin and 10 µg/ml recombinant IL-6. Antibodies 2F8, 4A5, 4E10 and 5F12 were purified by affinity chromatography using protein G-Sepharose according to the technique of Darby et al., J. Immunol. Methods, 1993 159 125-129, and the yield assessed by measuring absorption at 280 nm.

Example 5

Use of Monoclonal Antibodies to Human VEGF-D for Immunohistochemical Analysis of Human Tumors In order to assess the role of VEGF-D in tumorigenesis, the above described MAbs were used for immunohistochemical analysis of a human malignant melanoma. Four VEGF-D MAbs, 2F8, SF12, 4A5 and 4E10, were used for the analysis. A MAb raised to the receptor for granulocyte colony-stimulating factor, designated LMM774 (Layton et al., Growth Factors, 1997 14 117-130), was used as a negative control. Like the VEGF-D MAbs, LMM774 was of the mouse $IgG_1$ isotype and therefore served as an isotype-matched control antibody. The MAbs were tested against two randomly chosen invasive malignant melanomas by immunohistochemistry. Five micrometer thick sections from formalin fixed and paraffin embedded tissue of the cutaneous malignant melanomas were used as the test tissue. The sections were dewaxed and rehydrated and then washed with PBS. Normal rabbit serum diluted 1:50 was applied to each section for 20 minutes. The excess serum was blotted off and the primary antibodies, i.e. the VEGF-D MAbs and LMM774 at crudely optimized dilutions of 1:100 and 1:200, were applied to the sections and incubated in a moist chamber at room temperature overnight. The sections were again washed in PBS for 5 minutes followed by the application of biotinylated rabbit anti-mouse antibodies (DAKO Corp., Carpinteria, Calif.) at a 1:400 dilution in PBS for 35 minutes at room temperature. The sections were then washed in tris buffered saline (TBS) for 5 minutes and then streptavidin-alkaline phosphatase (Silenus, Australia) was applied at a 1:500 dilution in TBS. The sections were washed in TBS for 5 minutes and the fast red substrate (Sigma, St. Louis, Mo.) was applied at room temperature for 20 minutes. The sections were washed in water and then mounted. The red reaction product was used to avoid confusion in interpretation of those tumors producing melanin. A step omission control, in which the VEGF-D MAbs were omitted, was included as were isotype-matched controls with the LMM774 antibody.

Figure 7A:
FIGS. 7A-7E show the analysis of human malignant melanoma by immunohistochemistry with VEGF-D monoclonal antibodies.
Figure 7B:
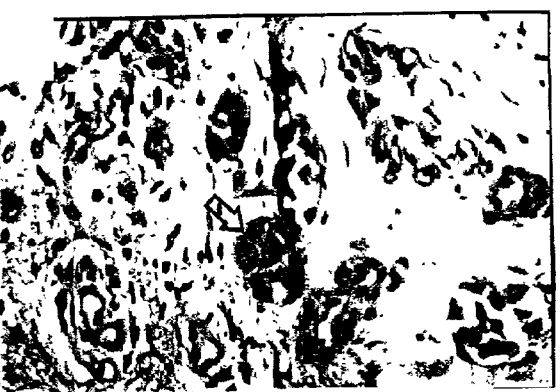
Figure 7C:
Figure 7D:
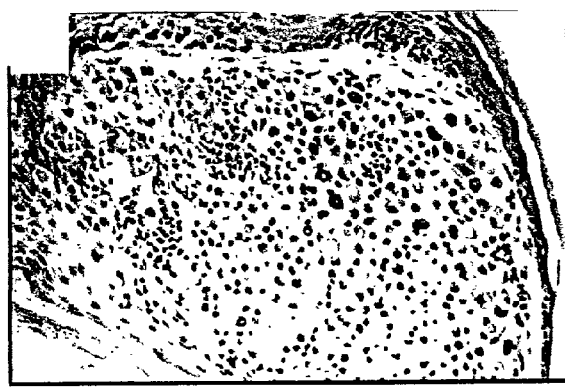
Figure 7E:

FIGS. 7A-C show results with the same melanoma sample whereas FIGS. 7D and 7E show results for a different tumor stained in the same batch. Islands of immunoreactive melanoma cells are indicated by a one (1) inside the arrows in FIGS. 7A and 7B, and immunoreactive blood vessels are indicated a two (2) inside the arrows in 7C. Melanoma cells with varying levels of VEGF-D are apparent in 7E. The magnification in FIGS. 7A, 7D and 7E is approximately ×60, and in FIGS. 7B and 7C, it is approximately ×300.

Positive reactions were seen with all four VEGF-D MAbs with essentially the same staining patterns. The results shown in FIGS. 7A-C and 7E were with MAb 2F8. Assessment of the staining patterns by light microscopic examination showed variable staining through the bulk of the melanomas. In the larger tumor, staining was more pronounced in small islands of tumor cells at the periphery of the invasive portions (FIGS. 7A and 7B) and in the intraepidermal nests of tumor cells, being less intense or undetectable in the central invasive portion of the tumor. Small capillary sized vessels in the papillary and reticular dermis adjacent to positive reacting tumor cells showed variable granular reaction to the antibodies in the cytoplasm of endothelial cells (FIG. 7C). The reaction for the smaller tumor was more even in distribution throughout the tumor mass (FIG. 7E). Blood vessels at a variable distance lateral to the tumor, and in the mid and deep reticular dermis and subcutaneous tissue away from the immunoreactive tumor cells did not show any reaction with the VEGF-D MAbs. In contrast to the results with the VEGF-D MAbs, the LMM774 control in the same tumor was negative (FIG. 7D) as were the step omission controls.

It has been shown for some tumors that VEGF synthesis and secretion can be switched on in hypoxic tumor cells and that the tumor can also induce expression of VEGFR-2 in the endothelial cells of nearby blood vessels (Plate et al., Cancer Res., 1993 53 5822-5827). In this way a paracrine system is established for inducing tumor angiogenesis whereby VEGF, secreted in the tumor, diffuses through interstitium and binds to VEGFR-2 on target endothelial cells and thereby induces endothelial cell proliferation. The results for VEGF-D localization in melanomas indicate that VEGF-D may be fulfilling a similar function in malignant melanomas. The VEGF-D MAbs detected VEGF-D in melanoma cells in both clinical samples tested. These tumor cells are most likely producing VEGF-D. In addition, VEGF-D was detected on the endothelial cells of blood vessels in the vicinity of the producer tumor cells but not on more distant vessels. The VEGF-D is probably localized on these endothelial cells due to interaction with VEGFR-2, a receptor for VEGF-D which is often expressed on tumor blood vessels (Plate et al., Cancer Res., 1993 53 5822-5827). Further immunohistochemical analyses will be required to assess if VEGF-D is also localized on lymphatic vessels in the vicinity of the tumor. Such a scenario is feasible because lymphatic endothelial cells express VEGFR-3, a high affinity receptor for VEGF-D (Joukov et al., The EMBO Journal, 1996 15 290-298).

The results indicate that melanoma cells can express the VEGF-D gene. Analysis of mouse embryos at post-coital day 15.5 by in situ hybridization showed expression of the VEGF-D gene immediately under the developing skin, in a region rich in developing melanocytes and fibroblasts (Example 3 and FIGS. 5 and 6). Therefore it may be that transformed melanocytes have re-acquired the capacity to express the gene for VEGF-D, as was the case during embryogenesis. If events other than oncogenic transformation can induce VEGF-D gene expression in melanocytes, this protein could be involved in other types of skin disorders characterized by inflammation or proliferation of blood vessels and/or lymphatic vessels. In a therapeutic setting, the application of VEGF-D in response to tissue damage may be useful for stimulating the growth of blood and lymphatic vessels adjacent to regenerating skin. Similarly, application of VEGF-D to stimulate angiogenesis and lymphangiogenesis is useful to enhance the success of skin grafting procedures. These are used in the treatment of a variety of conditions such as burns and other traumatic injuries, in avoiding or reducing surgical scarring, in cosmetic surgery, and the like.

Example 6

Testing Antibodies for the Capacity to Bind to VEGF-C

The enzyme immunoassay as described above was used to test the six VEGF-D MAbs for the capacity to bind to VEGF-CΔNΔC. VEGF-CΔNΔC consists of the VEGF homology domain of VEGF-C (residues 103 to 215) and is the region of VEGF-C which is most similar to VEGF-DΔNΔC. VEGF-CΔNΔC, to which a 6× histidine tag had been added at the C-terminus, was expressed in strain GS115 of the yeast *P. pastoris* using the expression vector pIC9 (Invitrogen, San Diego, Calif.) according to manufacturer's instructions and purified using Ni-NTA Superflow resin (QIAGEN, Valencia, Calif.) Of the six antibodies tested by this immunoassay, only 4E10 bound to VEGF-CΔNΔC.

Example 7

VEGF-D is Proteolytically Processed in a Similar Fashion to VEGF-C

Figure 8:
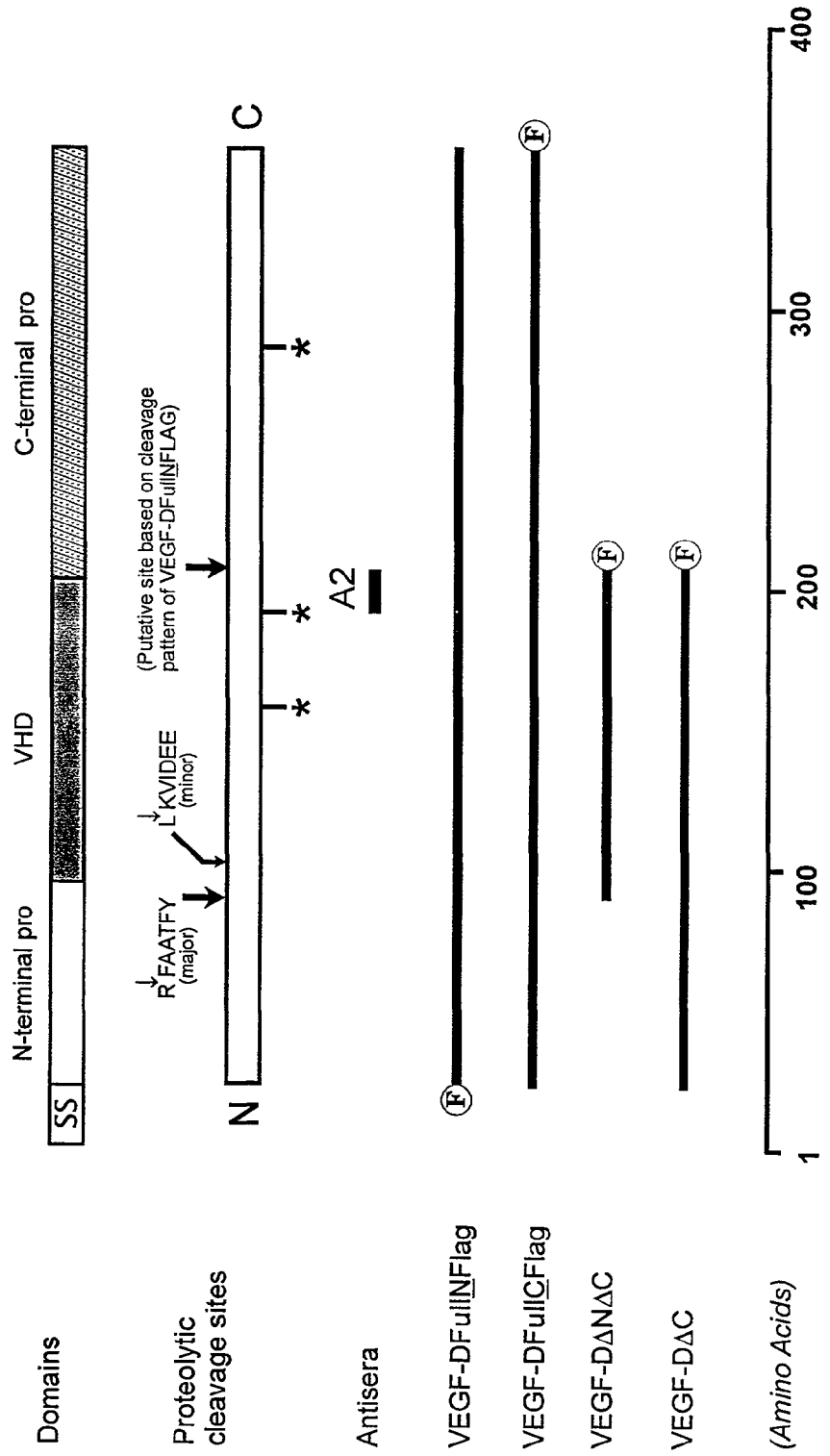
FIG. 8 provides a schematic representation of the structural domains of VEGF-D and some VEGF-D derivatives
Figure 9:
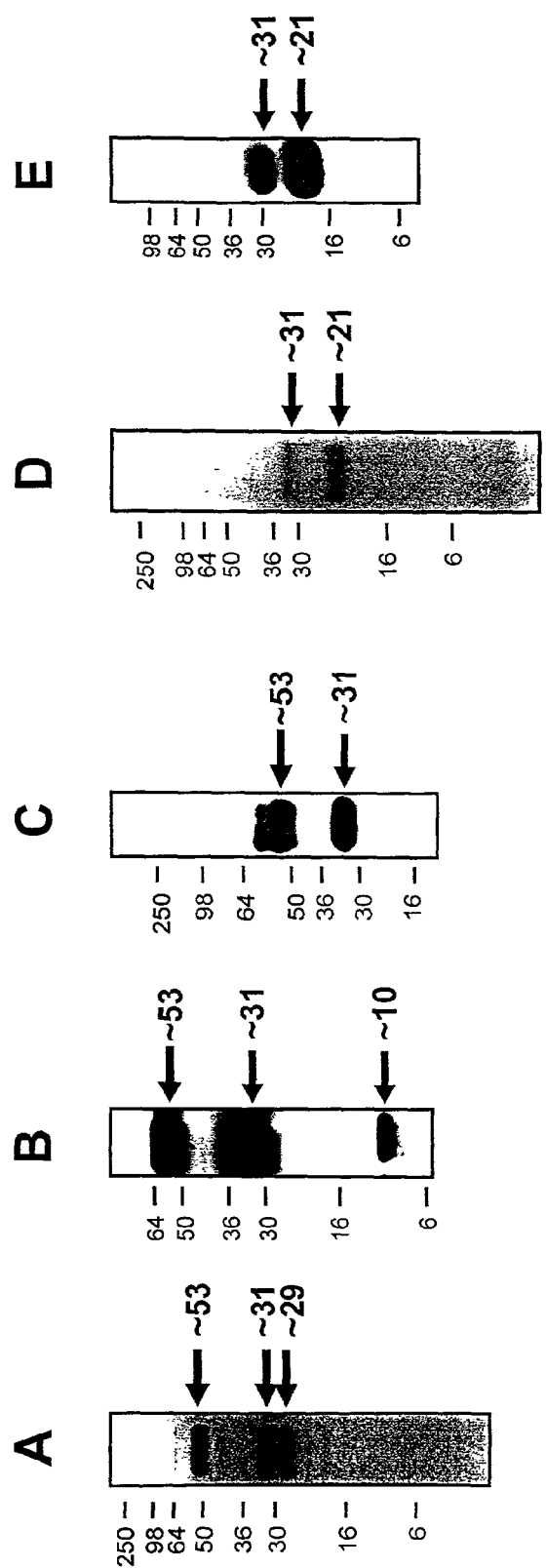
FIGS. 9A-9E show the analyses of VEGF-D derivatives secreted by 293-EBNA cells expressing VEGF-DFullNFlag (FIGS. 9A, 9B and 9C) and VEGF-DΔC (FIGS. 9D and 9E)

In order to investigate the proteolytic processing of VEGF-D, 293-EBNA cells were stably transfected with pVDApexΔC, pVDApexFullNFlag, pVDApexΔNΔC (Example 1 and FIG. 1) and pVDApexFullCFlag. These expression constructs encode VEGF-DΔC, VEGF-DFullNFlag, VEGF-DΔNΔC (Example 1 and FIG. 1) and VEGF-DFullCFlag respectively (FIG. 8). The VEGF-D structural domains are shown at the top of FIG. 8. "SS" denotes the signal sequence for protein secretion, N-terminal pro and C-terminal pro denote the propeptides and VHD denotes the VEGF homology domain. Beneath are shown the characterized and putative proteolytic cleavage sites in VEGF-D marked by arrows. The potential N-linked glycosylation sites are marked with asterisks. The region of VEGF-D used as the immunogen to generate the A2 antiserum (described below) is shown by a black bar. The bottom half of the figure shows the primary translation products for the VEGF-D derivatives expressed in 293-EBNA cells. For simplicity, the signal sequences for protein secretion have been omitted. The FLAG octapeptide epitope is denoted by an a similar fashion as pVDApexFullNFlag (Example 1) except that the DNA for the endogenous VEGF-D signal sequence for protein secretion had been retained and the "Kozak" consensus sequence for translation initiation had been optimized which necessitated insertion of the three amino acids "A-R-L" immediately after the initiation codon of VEGF-D. This construct also encoded the amino acids "A-R-Q" followed by the FLAG octapeptide sequence at the C-terminus of the protein. Since the 293-EBNA cell line is capable of proteolytically processing VEGF-C (Joukov et al., EMBO J., 1997 16 3898-3911), this allows analysis of the VEGF-D derivatives derived from these transfected cells to be followed during cellular biosynthesis and processing.

The VEGF-D derivatives were purified from the conditioned medium of stably transfected 293-EBNA cells by affinity chromatography on M2 (anti-FLAG) gel (Sigma-Aldrich) and eluted using the FLAG® peptide according to the manufacturer. The FLAG® peptide was removed using a centrifugal concentrator (Amicon, Beverly, Mass.). Aliquots of the fractions eluted from the M2 affinity columns were analyzed by SDS-PAGE and silver staining or immunoblotted with the M2 antibody (Sigma-Aldrich) to confirm the identity of the purified species.

Figure 11:
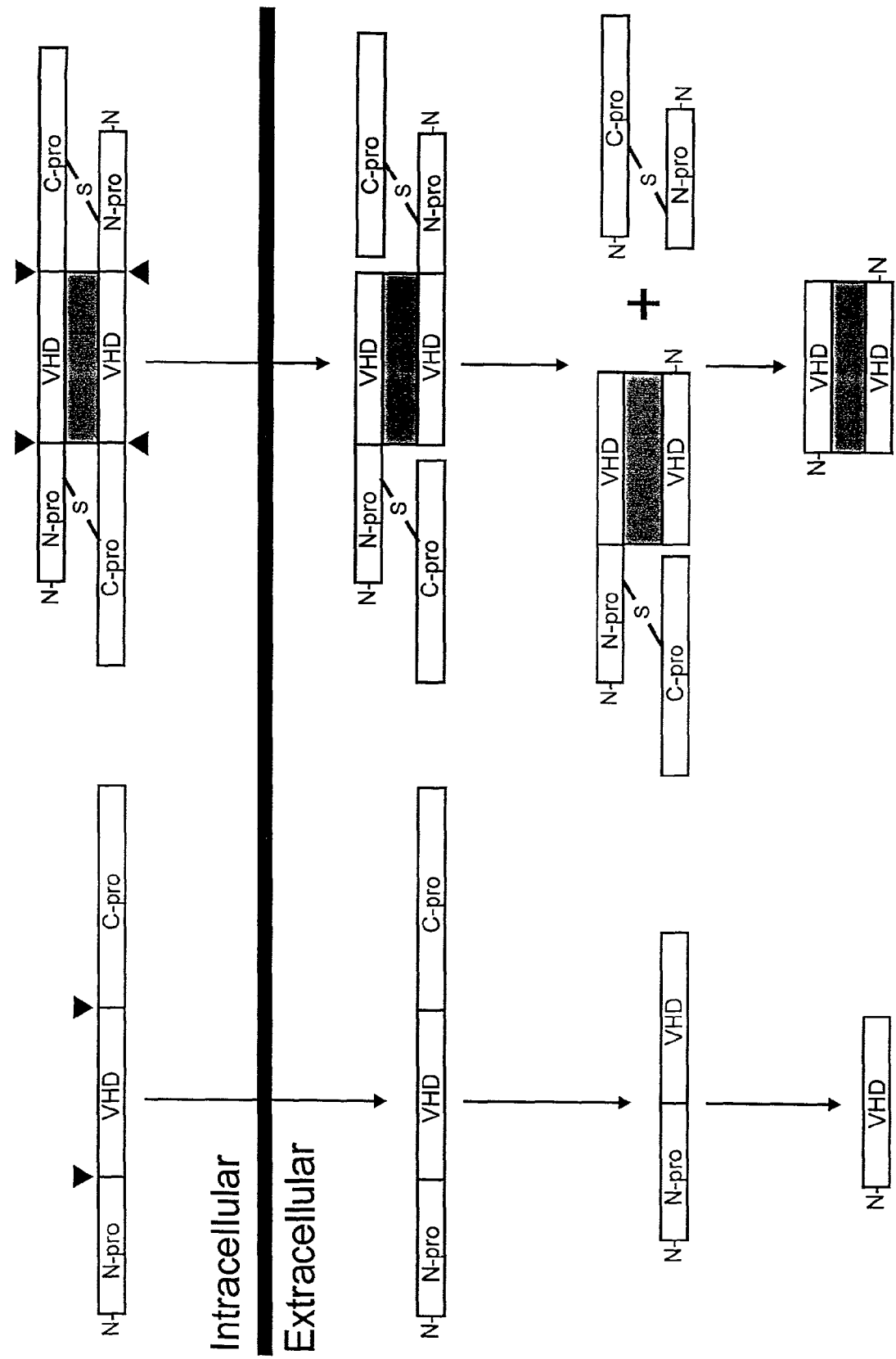
FIG. 11 provides a schematic representation of the mode of VEGF-D processing.

Analysis of the 293-EBNA cells expressing the various VEGF-D derivatives by SDS-PAGE show that the VEGF-D polypeptide is proteolytically processed. Purification using medium from 293-EBNA cells expressing VEGF-DFullN-Flag allowed specific analysis of only those VEGF-D polypeptides with the FLAG octapeptide at the N-terminus or of derivatives bound covalently or non-covalently to the FLAG®-tagged polypeptides (FIG. 8 and FIG. 11).

The polyclonal antiserum designated A2 was raised in rabbits against a synthetic peptide corresponding to the region of human VEGF-D from residues 190 to 205, KCLPTAPRHPYSIIRR (SEQ ID NO:3), which are in the VHD (SEQ ID NO:11).

For the SDS-PAGE and Western Blot analysis, samples containing the purified VEGF-D derivatives were combined 1:1 with 2×SDS-PAGE sample buffer, boiled and resolved by SDS-PAGE (Laemmli, Nature, 1970 227 680-685). The proteins were then transferred to an Immobilon-P membrane (Millipore, Bedford, Mass.) and non-specific binding sites were blocked by incubation in 3% BSA, 100 mM Tris-HCl (pH 7.5), 150 mM NaCl and 0.02% Tween 20. Blots were then incubated with a 1:2000 dilution of A2 antiserum for 2 hours at room temperature or alternatively with the M2 (anti-FLAG) antibody as described by the manufacturer. After washing in buffer (3% BSA, 100 mM Tris-HCl (pH 7.5), 150 mM NaCl and 0.02% Tween 20) the blots were probed with anti-rabbit Ig horseradish peroxidase (HRP) conjugate or anti-mouse Ig HRP conjugate (Biorad, Hercules, Calif.) and developed using chemiluminescence (ECL, Amersham, UK).

Analysis of proteins secreted by cells expressing VEGF-DFullNFlag by SDS-PAGE under reducing conditions and silver staining revealed a species of approximately 53 kDa, the expected size of unprocessed VEGF-D, as well as two polypeptides of approximately 31 and 29 kDa (FIG. 9A) The sizes of molecular weight markers (in kDa) are shown to the left of each panel and the positions of the VEGF-D derivatives (with molecular weights in kDa) are marked by arrows to the right. This result is consistent with proteolytic cleavage events occurring near the C-terminus of the VHD. According to this model, the approximately 53 kDa polypeptide would represent unprocessed VEGF-D and the approximately 31 kDa polypeptide would consist of the N-terminal propeptide and the VHD (i.e. lacking the C-terminal propeptide). The expected size of a polypeptide consisting of the N-terminal propeptide and the VHD is indeed approximately 31 kDa because the VHD, which is glycosylated, was shown previously to be approximately 21 kDa (Achen et al., Proc. Natl. Acad. Sci. USA, 1998 95 548-553; FIG. 12b of PCT/US97/14696) and the expected size of the FLAG-tagged N-terminal extension is approximately 10 kDa. If processing of VEGF-D involves cleavage near the N-terminus of the VHD, in addition to the C-terminus of the VHD, cells expressing VEGF-DFullNFlag should also secrete a 10 kDa FLAG-tagged polypeptide consisting only of the N-terminal extension. Although a 10 kDa polypeptide was not detected among the VEGF-D derivatives secreted by these cells as assessed by silver staining (FIG. 9A), it was clearly detected by Western blot analysis of the same material using the M2 antibody (FIG. 9B). The approximately 29 kDa polypeptide detected by silver staining was not detected in the same sample by Western blot with the A2 polyclonal antiserum (FIG. 9C) and therefore would represent the C-terminal propeptide. This was confirmed by N-terminal amino acid of this polypeptide which identified the N-terminal sequence as "SIQIPEED" (SEQ ID NO:4), which is immediately adjacent to the predicted C-terminal cleavage site of the VHD based on comparison with VEGF-C. Therefore the C-terminal cleavage site in VEGF-D is located immediately after arginine 205 ("R↓SIQIPEED") (SEQ ID NO:5). It is most likely that this approximately 29 kDa polypeptide was present in the affinity-purified material because of the interchain disulfide bonds between the—and C-terminal propeptides (see FIG. 11 for a scheme for VEGF-D processing).

To further examine the possibility of proteolytic cleavage of VEGF-D near the N-terminus of the VHD, proteins secreted by 293-EBNA cells expressing VEGF-DΔC were purified and analyzed as above. The construct for VEGF-DΔC drives expression of a VEGF-D derivative in which the C-terminal extension has been deleted and replaced with FLAG (FIG. 8). Conditioned medium from these cells contained two FLAG-tagged polypeptides of approximately 31 and 21 kDa as assessed by silver staining (FIG. 9D). This result is consistent with an N-terminal cleavage event which occurs near the N-terminus of the VHD, approximately 10 kDa from the N-terminus of unprocessed VEGF-D. Thus the approximately 31 kDa polypeptide would consist of the N-terminal extension and the VHD, whereas the approximately 21 kDa polypeptide would consist of the VHD alone. Consistent with this model were the findings that the both the approximately 31 and approximately 21 kDa bands were detected by Western blot analysis with M2 antibody (FIG. 9E). Also as expected, both bands were detected by Western blot analysis with the A2 antiserum (data not shown).

To determine the exact position of the N-terminal proteolytic cleavage site in VEGF-D, the approximately 21 kDa polypeptide purified from the supernatants of cells expressing VEGF-DΔC was subjected to N-terminal amino acid sequencing. N-terminal amino acid sequencing of affinity-purified protein was carried out using a Hewlett-Packard Protein Sequencer, model G1000A (Hewlett-Packard, Palo Alto, Calif.). The N-terminal sequence of this polypeptide was heterogeneous. The predominant sequence, representing approximately 80% of the material began as "FAATFY" (SEQ ID NO:6) and a minor sequence, representing 10-15% of the material began with "KVIDEE" (SEQ ID NO:7). Thus, as expected, the N-terminus of the approximately 21 kDa polypeptide is located at about the same position as the N-terminus of the VHD. The major N-terminal cleavage site in VEGF-D is located immediately after arginine 88 ("R↓FAATFY") (SEQ ID NO:8) and the minor cleavage site is immediately after leucine 99 (L↓SKVIDEE) (SEQ ID NO:9) (FIG. 8).

Example 8

VEGF-DΔNΔC Exists Predominantly in the Form of a Non-Covalent Dimer

In general, VEGF family members exist as disulfide-bonded homodimers. However, VEGF-CΔNΔC exists predominantly in the form of a non-covalent dimer (Joukov et al., EMBO J., 1997 16 3898-3911). The mature form of VEGF-D, VEGF-DΔNproΔCpro, is also not a disulfide-linked dimer because this polypeptide migrates almost identically under reducing and non-reducing conditions in SDS-PAGE. In order to test the nature of the mature form of VEGF-D, affinity-purified VEGF-DΔNΔC was subjected to size exclusion chromatography. Size exclusion chromatography was carried out by loading the affinity-purified protein onto a TSKG2000SW (7.5×60 mm Id) column (LKB Bromo, Sweden). The column was equilibrated with PBS. Proteins were eluted with a flow rate of 0.25 ml/min and 1 minute fractions collected. The protein elution was monitored at 215 nm. Three major peaks were eluted from the column with apparent molecular weights (shown above each peak in brackets) of 73 kDa (peak 1), 49 kDa (peak 2) and 25 kDa (peak 3) and the ratio of total protein in these peaks was estimated spectrophotometrically to be approximately 1:2.1:0.9 (FIG. 10A). The apparent molecular weights were determined using a calibration curve constructed from known proteins: bovine serum albumin dimer, bovine serum albumin, ovalbumin and trypsin inhibitor (Sigma Aldrich Pty Ltd, Australia). The fractions corresponding to these peaks were pooled, concentrated to 100 μl using centrifugal concentrators and analyzed by SDS-

Figure 10A:
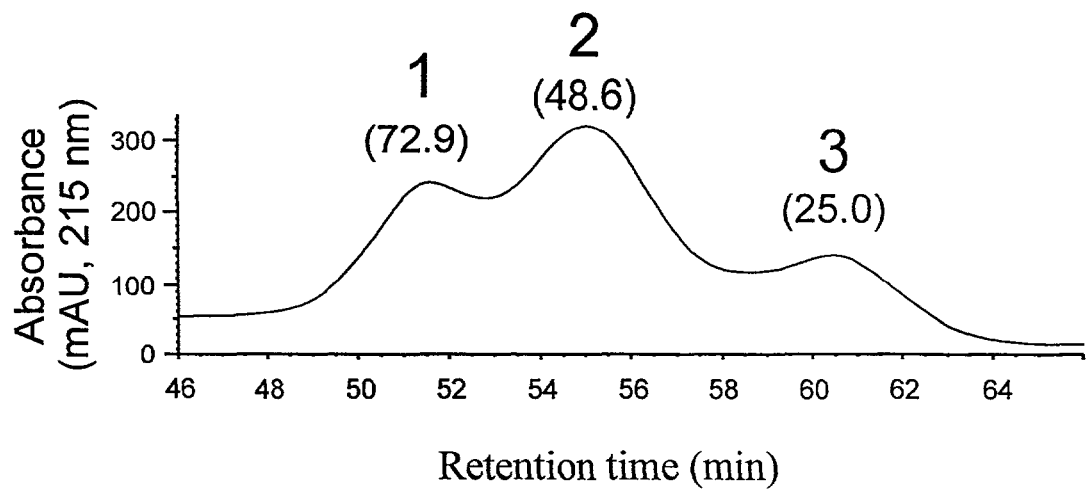
FIGS. 10A and 10B show the analysis of VEGF-DΔNΔC by size exclusion chromatography and SDS-PAGE.
Figure 10B:

PAGE under reducing conditions and silver stained (FIG. 10B). Tracks 1, 2 and 3 correspond to protein from peaks 1, 2 and 3 respectively. The position of the VEGF-DΔNΔC subunit is shown in FIG. 10B to the left and the positions of molecular weight markers (in kDa) are shown to the right.

The VEGF-DΔNΔC subunit (approximately 21 kDa) was most abundant in peak 2, was easily detectable in peak 3 and was undetectable from peak 1 (FIG. 10B). The predominant species in peak 1 was a 73 kDa protein which is a contaminant that is often detected in samples of protein purified by M2 affinity chromatography and which cannot be detected by Western blot analysis with either M2 antibody or A2 antiserum (data not shown). The 73 kDa protein was also observed in control M2 affinity purifications using the supernatants from 293-EBNA cells which had been transfected with Apex-3 plasmid lacking sequence encoding VEGF-D (data not shown). The apparent molecular weights determined from the size exclusion chromatography indicated that the proteins in peaks 2 and 3 were a VEGF-DΔNΔC dimer and the VEGF-DΔNΔC monomer respectively. Therefore, a non-covalent dimer, the subunits of which separate in SDS-PAGE under reducing or non-reducing conditions, was the predominant molecular species in the affinity-purified preparations of VEGF-DΔNΔC.

The capacities of the dimeric and monomeric forms of VEGF-DΔNΔC to bind VEGFR-2 were assessed with fractions eluted from the column and assaying for the capacity to bind VEGFR-2 using the Ba/F3 cell bioassay described in International Patent application PCT/US95/16755. The VEGFR-2-binding activity in peak 3 was approximately 2% of that in peak 2, indicating that the VEGF-DΔNΔC non-covalent homodimer is much more bioactive than the monomer. The VEGFR-2 binding activity in peak 1 was approximately 1% of that in peak 2, presumably reflecting a small amount of the VEGF-DΔNΔC non-covalent homodimer in this peak. Clearly the dimeric form of VEGF-DΔNΔC binds far better to VEGFR-2 than does the monomeric form.

The data presented in Example 6 demonstrates that VEGF-D is proteolytically processed and that the sites of proteolytic cleavage are similar in location, but not identical, to those in VEGF-C. The proteolytic processing is likely to be of considerable biological importance because different VEGF-D derivatives have different capacities for activating VEGF receptors. Whereas fully processed VEGF-D binds and activates both VEGFR-2 and VEGFR-3 (Achen et al., Proc. Natl. Acad. Sci. USA, 1998 95 548-553) the unprocessed form of VEGF-D activates VEGFR-3 but not VEGFR-2 (FIGS. 14 and 15 of PCT/US97/14696). Therefore step-wise proteolytic processing may be a way to regulate the receptor-binding specificity of VEGF-D in vivo.

Size exclusion chromatography also demonstrated that affinity-purified VEGF-DΔNΔC is predominantly a non-covalent dimer but that a small proportion is monomeric. Only the dimeric form could strongly activate a chimeric receptor containing the extracellular domain of VEGFR-2. This finding was expected, given that activation of cell surface receptor tyrosine kinases involves receptor dimerization. Presumably the dimeric ligand provides two receptor binding sites per molecule whereas the monomeric form provides only one: Thus the dimeric ligand can induce receptor dimerization but the monomeric ligand cannot.

A scheme for the processing of VEGF-D as carried out by 293-EBNA cells which would give rise to monomers and dimers is shown in FIG. 11. Two distinct forms of unprocessed VEGF-D are secreted from the cell: a monomer (left side) and an anti-parallel disulfide-linked dimer with disulfide bridges between the—and C-terminal propeptides (right side). Arrows lead from the intracellular forms to the products of stepwise proteolytic processing at the—and C-termini of the VHD which ultimately give rise to mature forms of VEGF-D that consist of a non-covalent dimer and a monomer of the VHD. Analyses of VEGF-D derivatives from the cell lines described here suggest that cleavage of the C-terminal propeptide from the VHD is more efficient than cleavage of the N-terminal propeptide. For simplicity, not all possible derivatives arising from proteolytic processing are shown. In FIG. 11, N-pro denotes N-terminal propeptide; C-pro, the C-terminal propeptide; VHD, the VEGF homology domain; grey boxes, non-covalent interactions between domains; —S—, intersubunit disulfide bridges; N—, the N-termini of polypeptides; and the arrowheads represent the approximate locations of proteolytic cleavage sites.

Example 9

VEGF-D and Vascular Permeability

Affinity-purified human VEGF-DΔNΔC was tested for the capacity to induce vascular permeability using the Miles assay. The Miles assay (Miles, A. A. and Miles, E. M., J. Physiol., 1952 118 228-257) was performed using anesthetized guinea pigs. For quantitation of extravasation induced by permeability factors, the area of sample injection was excised and the Evans Blue dye extracted by a three day incubation in formamide at 42.degree. C. The amount of dye extracted was quantitated spectrophotometrically by reading the absorbance of the samples at 620 nm. VEGF-DΔNΔC was used because the VHD of human VEGF-C (VEGF-CΔNΔC) is known to induce vascular permeability (Joukov et al., EMBO J., 1997 16 3898-3911). Purified mouse VEGF$_{164}$ was included as a positive control. As expected, mouse VEGF$_{164}$ strongly induced vascular permeability. The lowest concentration of mouse VEGF$_{164}$ which induced detectable vascular permeability was 60 ng/ml. Likewise, human VEGF-CΔNΔC also induced vascular permeability, however the lowest concentration with detectable activity was 250 ng/ml. In contrast, VEGF-DΔNΔC showed no activity, even at protein concentrations as high as 1 μg/ml. These results indicate that human VEGF-DΔNΔC is not an inducer of vascular permeability in guinea pigs.

VEGF-D and VEGF-C are considered members of a subfamily of the VEGF family (Achen et al., Proc. Natl. Acad. Sci. USA, 1998 95 548-553) because of similarities in primary structure and receptor-binding specificity. The mechanisms of processing of these two molecules are similar, but not identical. However, these two growth factors exhibit differences in bioactivities as illustrated by the finding that VEGF-DΔNΔC does not induce vascular permeability. In contrast, VEGF-CΔNΔC does induce vascular permeability although not as potently as VEGF (Joukov et al., EMBO J., 1997 16 3898-3911).

The foregoing description and examples have been set forth merely to illustrate the invention and are not intended to be limiting. Since modifications of the disclosed embodiments incorporating the spirit and substance of the invention may occur to persons skilled in the art, the invention should be construed broadly to include all variations falling within the scope of the appended claims and equivalents thereof.

SEQUENCE LISTING

<160> NUMBER OF SEQ ID NOS: 15

<210> SEQ ID NO 1
<211> LENGTH: 109
<212> TYPE: PRT
<213> ORGANISM: Homo sapiens

<400> SEQUENCE: 1

Phe Tyr Asp Ile Glu Thr Leu Lys Val Ile Asp Glu Glu Trp Gln Arg
1               5                   10                  15

Thr Gln Cys Ser Pro Arg Glu Thr Cys Val Glu Val Ala Ser Glu Leu
            20                  25                  30

Gly Lys Ser Thr Asn Thr Phe Phe Lys Pro Pro Cys Val Asn Val Phe
        35                  40                  45

Arg Cys Gly Gly Cys Cys Asn Glu Glu Ser Leu Ile Cys Met Asn Thr
    50                  55                  60

Ser Thr Ser Tyr Ile Ser Lys Gln Leu Phe Glu Ile Ser Val Pro Leu
65                  70                  75                  80

Thr Ser Val Pro Glu Leu Val Pro Val Lys Val Ala Asn His Thr Gly
                85                  90                  95

Cys Lys Cys Leu Pro Thr Ala Pro Arg His Pro Tyr Ser
            100                 105

<210> SEQ ID NO 2
<211> LENGTH: 1325
<212> TYPE: DNA
<213> ORGANISM: Homo sapiens

<400> SEQUENCE: 2
ggagaatgcc ttttgcaaca cttttcagta gctgcctgga acaactgct tagtcatcgg      60 tagacattta aaatattcaa aatgtatgga gaatggggaa tggggaatat cctcatgatg    120
ttccatgtgt acttggtgca gggcttcagg agcgaacatg gaccagtgaa ggattttct    180 tttgagcgat catcccggtc catgttggaa cgatctgaac aacagatccg agcagcttct    240
agtttggagg agttgctgca aatcgcgcac tctgaggact ggaagctgtg gcgatgccgg    300
ttgaagctca aaagtcttgc cagtatggac tcacgctcag catcccatcg ctccaccaga    360
tttgcggcaa cttctatga cactgaaaca ctaaaagtta tagatgaaga atggcagagg    420
acccaatgca gccctagaga gacatgcgta gaagtcgcca gtgagctggg gaagacaacc    480
aacacattct tcaagccccc ctgtgtaaat gtcttccggt gtggaggctg ctgcaacgaa    540
gagggtgtga tgtgtatgaa cacaagcacc tcctacatct ccaaacagct ctttgagata    600
tcagtgcctc tgacatcagt gcccgagtta gtgcctgtta aaattgccaa ccatacgggt    660
tgtaagtgct tgcccacggg ccccgccat cctactcaa ttatcagaag atccattcag    720
accccagaag aagatgaatg tcctcattcc aagaaactct gtcctattga catgctgtgg    780
gataacacca atgtaaatg tgttttgcaa gacgagactc cactgcctgg gacagaagac    840
cactcttacc tccaggaacc cactctctgt ggaccgcaca tgacgtttga tgaagatcgc    900
tgtgagtgcg tctgtaaagc accatgtccg ggagatctca ttcagcaccc ggaaaactgc    960
agttgctttg agtgcaaaga aagtctggag agctgctgcc aaaagcacaa gattttcac    1020 ccagacacct gcagctgtga ggacagatgt ccttttcaca ccagaacatg tgcaagtaga    1080
aagccagcct gtgaaaagca ctggcgcttt ccaaaggaga caagggccca gggactctac    1140
agccaggaga acccttgatt caacttcctt tcaagtcccc ccatctctgt cattttaaac    1200

```
agctcactgc tttgtcaagt tgctgtcact gttgcccact accccttgaa catgtgcaaa    1260
cacagacaca cacacacaca cacacacaga gcaactagga ttatgttttc taggtgctgc    1320
ctaag                                                                1325
```

<210> SEQ ID NO 3
<211> LENGTH: 320
<212> TYPE: PRT
<213> ORGANISM: Homo sapiens

<400> SEQUENCE: 3

```
Met Tyr Gly Glu Trp Gly Met Gly Asn Ile Leu Met Met Phe His Val
1               5                  10                  15

Tyr Leu Val Gln Gly Phe Arg Ser Glu His Gly Pro Val Lys Arg Ser
            20                  25                  30

Ser Arg Ser Met Leu Glu Arg Ser Glu Gln Gln Ile Arg Ala Ala Ser
        35                  40                  45

Ser Leu Glu Glu Leu Leu Gln Ile Ala His Ser Glu Asp Trp Lys Leu
    50                  55                  60

Trp Arg Cys Arg Leu Lys Leu Lys Ser Leu Ala Ser Met Asp Ser Arg
65                  70                  75                  80

Ser Ala Ser His Arg Ser Thr Arg Phe Ala Ala Thr Phe Tyr Asp Thr
                85                  90                  95

Glu Thr Leu Lys Val Ile Asp Glu Gly Trp Gln Arg Thr Gln Cys Ser
            100                 105                 110

Pro Arg Glu Thr Cys Val Glu Val Ala Ser Glu Leu Gly Lys Thr Thr
        115                 120                 125

Asn Thr Phe Phe Lys Pro Pro Cys Val Asn Val Phe Arg Cys Gly Gly
    130                 135                 140

Cys Cys Asn Glu Glu Gly Val Met Cys Met Asn Thr Ser Thr Ser Tyr
145                 150                 155                 160

Ile Ser Lys Gln Leu Phe Glu Ile Ser Val Pro Leu Thr Ser Val Pro
                165                 170                 175

Glu Leu Val Pro Val Lys Ile Ala Asn His Thr Gly Cys Lys Cys Leu
            180                 185                 190

Pro Thr Gly Pro Arg His Pro Tyr Ser Ile Ile Arg Arg Ser Ile Gln
        195                 200                 205

Thr Pro Glu Glu Asp Glu Cys Pro His Ser Lys Lys Leu Cys Pro Ile
    210                 215                 220

Asp Met Leu Trp Asp Asn Thr Lys Cys Lys Cys Val Leu Gln Asp Glu
225                 230                 235                 240

Thr Pro Leu Pro Gly Thr Glu Asp His Ser Tyr Leu Gln Glu Pro Thr
                245                 250                 255

Leu Cys Gly Pro His Met Thr Phe Asp Glu Asp Arg Cys Glu Cys Val
            260                 265                 270

Cys Lys Ala Pro Cys Pro Gly Asp Leu Ile Gln His Pro Glu Asn Cys
        275                 280                 285

Ser Cys Phe Glu Cys Lys Glu Ser Leu Glu Ser Cys Cys Gln Lys His
    290                 295                 300

Lys Ile Phe His Pro Asp Thr Cys Arg Ser Met Val Phe Ser Leu Ser
305                 310                 315                 320
```

<210> SEQ ID NO 4
<211> LENGTH: 8
<212> TYPE: PRT
<213> ORGANISM: Homo sapiens

<400> SEQUENCE: 4

Ser Ile Gln Ile Pro Glu Glu Asp
1               5

<210> SEQ ID NO 5
<211> LENGTH: 9
<212> TYPE: PRT
<213> ORGANISM: Homo sapiens

<400> SEQUENCE: 5

Arg Ser Ile Gln Ile Pro Glu Glu Asp
1               5

<210> SEQ ID NO 6
<211> LENGTH: 6
<212> TYPE: PRT
<213> ORGANISM: Homo sapiens

<400> SEQUENCE: 6

Phe Ala Ala Thr Phe Tyr
1               5

<210> SEQ ID NO 7
<211> LENGTH: 6
<212> TYPE: PRT
<213> ORGANISM: Homo sapiens

<400> SEQUENCE: 7

Lys Val Ile Asp Glu Glu
1               5

<210> SEQ ID NO 8
<211> LENGTH: 7
<212> TYPE: PRT
<213> ORGANISM: Homo sapiens

<400> SEQUENCE: 8

Arg Phe Ala Ala Thr Phe Tyr
1               5

<210> SEQ ID NO 9
<211> LENGTH: 7
<212> TYPE: PRT
<213> ORGANISM: Homo sapiens

<400> SEQUENCE: 9

Leu Lys Val Ile Asp Glu Glu
1               5

<210> SEQ ID NO 10
<211> LENGTH: 354
<212> TYPE: PRT
<213> ORGANISM: Homo sapiens

<400> SEQUENCE: 10

Met Tyr Arg Glu Trp Val Val Asn Val Phe Met Met Leu Tyr Val
1               5                   10                  15

Gln Leu Val Gln Gly Ser Ser Asn Glu His Gly Pro Val Lys Arg Ser
            20                  25                  30

Ser Gln Ser Thr Leu Glu Arg Ser Glu Gln Gln Ile Arg Ala Ala Ser
        35                  40                  45

Ser Leu Glu Glu Leu Leu Arg Ile Thr His Ser Glu Asp Trp Lys Leu
    50                  55                  60

```
Trp Arg Cys Arg Leu Arg Leu Lys Ser Phe Thr Ser Met Asp Ser Arg
 65                  70                  75                  80

Ser Ala Ser His Arg Ser Thr Arg Phe Ala Ala Thr Phe Tyr Asp Ile
                 85                  90                  95

Glu Thr Leu Lys Val Ile Asp Glu Glu Trp Gln Arg Thr Gln Cys Ser
            100                 105                 110

Pro Arg Glu Thr Cys Val Glu Val Ala Ser Glu Leu Gly Lys Ser Thr
        115                 120                 125

Asn Thr Phe Phe Lys Pro Pro Cys Val Asn Val Phe Arg Cys Gly Gly
    130                 135                 140

Cys Cys Asn Glu Glu Ser Leu Ile Cys Met Asn Thr Ser Thr Ser Tyr
145                 150                 155                 160

Ile Ser Lys Gln Leu Phe Glu Ile Ser Val Pro Leu Thr Ser Val Pro
                165                 170                 175

Glu Leu Val Pro Val Lys Val Ala Asn His Thr Gly Cys Lys Cys Leu
            180                 185                 190

Pro Thr Ala Pro Arg His Pro Tyr Ser Ile Ile Arg Arg Ser Ile Gln
        195                 200                 205

Ile Pro Glu Glu Asp Arg Cys Ser His Ser Lys Lys Leu Cys Pro Ile
    210                 215                 220

Asp Met Leu Trp Asp Ser Asn Lys Cys Lys Cys Val Leu Gln Glu Glu
225                 230                 235                 240

Asn Pro Leu Ala Gly Thr Glu Asp His Ser His Leu Gln Glu Pro Ala
                245                 250                 255

Leu Cys Gly Pro His Met Met Phe Asp Glu Asp Arg Cys Glu Cys Val
            260                 265                 270

Cys Lys Thr Pro Cys Pro Lys Asp Leu Ile Gln His Pro Lys Asn Cys
        275                 280                 285

Ser Cys Phe Glu Cys Lys Glu Ser Leu Glu Thr Cys Cys Gln Lys His
    290                 295                 300

Lys Leu Phe His Pro Asp Thr Cys Ser Cys Glu Asp Arg Cys Pro Phe
305                 310                 315                 320

His Thr Arg Pro Cys Ala Ser Gly Lys Thr Ala Cys Ala Lys His Cys
                325                 330                 335

Arg Phe Pro Lys Glu Lys Arg Ala Ala Gln Gly Pro His Ser Arg Lys
            340                 345                 350

Asn Pro

<210> SEQ ID NO 11
<211> LENGTH: 352
<212> TYPE: PRT
<213> ORGANISM: Homo sapiens

<400> SEQUENCE: 11

Met Tyr Arg Glu Trp Val Val Asn Val Phe Met Met Leu Tyr Val
 1               5                  10                  15

Gln Leu Val Gln Gly Ser Ser Asn Glu His Gly Pro Val Lys Arg Ser
            20                  25                  30

Ser Gln Ser Thr Leu Glu Arg Ser Glu Gln Gln Ile Arg Ala Ala Ser
        35                  40                  45

Ser Leu Glu Glu Leu Leu Arg Ile Thr His Ser Glu Asp Trp Lys Leu
    50                  55                  60

Trp Arg Cys Arg Leu Arg Leu Lys Ser Phe Thr Ser Met Asp Ser Arg
 65                  70                  75                  80
```

```
Ser Ala Ser His Arg Ser Thr Arg Phe Ala Ala Thr Phe Tyr Asp Ile
            85                  90                  95

Glu Thr Leu Lys Val Ile Asp Glu Glu Trp Gln Arg Thr Gln Cys Ser
            100                 105                 110

Pro Arg Glu Thr Cys Val Glu Val Ala Ser Glu Leu Gly Lys Ser Thr
            115                 120                 125

Asn Thr Phe Phe Lys Pro Pro Cys Val Asn Val Phe Arg Cys Gly Gly
            130                 135                 140

Cys Cys Asn Glu Glu Ser Leu Ile Cys Met Asn Thr Ser Thr Ser Tyr
145                 150                 155                 160

Ile Ser Lys Gln Leu Phe Glu Ile Ser Val Pro Leu Thr Ser Val Pro
            165                 170                 175

Glu Leu Val Pro Val Lys Val Ala Asn His Thr Gly Cys Lys Cys Leu
            180                 185                 190

Pro Thr Ala Pro Arg His Pro Tyr Ser Ile Ile Arg Arg Ser Ile Gln
            195                 200                 205

Ile Pro Glu Glu Asp Arg Cys Ser His Ser Lys Lys Leu Cys Pro Ile
            210                 215                 220

Asp Met Leu Trp Asp Ser Asn Lys Cys Lys Cys Val Leu Gln Glu Glu
225                 230                 235                 240

Asn Pro Leu Ala Gly Thr Glu Asp His Ser His Leu Gln Glu Pro Ala
            245                 250                 255

Leu Cys Gly Pro His Met Met Phe Asp Glu Asp Arg Cys Glu Cys Val
            260                 265                 270

Cys Lys Thr Pro Cys Pro Lys Asp Leu Ile Gln His Pro Lys Asn Cys
            275                 280                 285

Ser Cys Phe Glu Cys Lys Glu Ser Leu Glu Thr Cys Cys Gln Lys His
            290                 295                 300

Lys Leu Phe His Pro Asp Thr Cys Ser Cys Glu Asp Arg Cys Pro Phe
305                 310                 315                 320

His Thr Arg Pro Cys Ala Ser Gly Lys Thr Ala Cys Ala Lys His Cys
            325                 330                 335

Arg Phe Pro Lys Glu Lys Arg Ala Ala Gln Gly Pro His Ser Arg Lys
            340                 345                 350

<210> SEQ ID NO 12
<211> LENGTH: 325
<212> TYPE: PRT
<213> ORGANISM: Homo sapiens

<400> SEQUENCE: 12

Met Arg Ser Ser Gln Ser Thr Leu Glu Arg Ser Glu Gln Gln Ile Arg
1               5                   10                  15

Ala Ala Ser Ser Leu Glu Glu Leu Leu Arg Ile Thr His Ser Glu Asp
            20                  25                  30

Trp Lys Leu Trp Arg Cys Arg Leu Arg Leu Lys Ser Phe Thr Ser Met
            35                  40                  45

Asp Ser Arg Ser Ala Ser His Arg Ser Thr Arg Phe Ala Ala Thr Phe
50                  55                  60

Tyr Asp Ile Glu Thr Leu Lys Val Ile Asp Glu Glu Trp Gln Arg Thr
65                  70                  75                  80

Gln Cys Ser Pro Arg Glu Thr Cys Val Glu Val Ala Ser Glu Leu Gly
            85                  90                  95

Lys Ser Thr Asn Thr Phe Phe Lys Pro Pro Cys Val Asn Val Phe Arg
            100                 105                 110
```

```
Cys Gly Gly Cys Cys Asn Glu Glu Ser Leu Ile Cys Met Asn Thr Ser
            115                 120                 125

Thr Ser Tyr Ile Ser Lys Gln Leu Phe Glu Ile Ser Val Pro Leu Thr
    130                 135                 140

Ser Val Pro Glu Leu Val Pro Val Lys Val Ala Asn His Thr Gly Cys
145                 150                 155                 160

Lys Cys Leu Pro Thr Ala Pro Arg His Pro Tyr Ser Ile Ile Arg Arg
                165                 170                 175

Ser Ile Gln Ile Pro Glu Glu Asp Arg Cys Ser His Ser Lys Lys Leu
                180                 185                 190

Cys Pro Ile Asp Met Leu Trp Asp Ser Asn Lys Cys Lys Cys Val Leu
            195                 200                 205

Gln Glu Glu Asn Pro Leu Ala Gly Thr Glu Asp His Ser His Leu Gln
    210                 215                 220

Glu Pro Ala Leu Cys Gly Pro His Met Met Phe Asp Glu Asp Arg Cys
225                 230                 235                 240

Glu Cys Val Cys Lys Thr Pro Cys Pro Lys Asp Leu Ile Gln His Pro
                245                 250                 255

Lys Asn Cys Ser Cys Phe Glu Cys Lys Glu Ser Leu Glu Thr Cys Cys
                260                 265                 270

Gln Lys His Lys Leu Phe His Pro Asp Thr Cys Ser Cys Glu Asp Arg
            275                 280                 285

Cys Pro Phe His Thr Arg Pro Cys Ala Ser Gly Lys Thr Ala Cys Ala
290                 295                 300

Lys His Cys Arg Phe Pro Lys Glu Lys Arg Ala Ala Gln Gly Pro His
305                 310                 315                 320

Ser Arg Lys Asn Pro
                325

<210> SEQ ID NO 13
<211> LENGTH: 358
<212> TYPE: PRT
<213> ORGANISM: Mus musculus

<400> SEQUENCE: 13

Met Tyr Gly Glu Trp Gly Met Gly Asn Ile Leu Met Met Phe His Val
1               5                   10                  15

Tyr Leu Val Gln Gly Phe Arg Ser Glu His Gly Pro Val Lys Asp Phe
            20                  25                  30

Ser Phe Glu Arg Ser Ser Arg Ser Met Leu Glu Arg Ser Glu Gln Gln
        35                  40                  45

Ile Arg Ala Ala Ser Ser Leu Glu Glu Leu Leu Gln Ile Ala His Ser
    50                  55                  60

Glu Asp Trp Lys Leu Trp Arg Cys Arg Leu Lys Leu Lys Ser Leu Ala
65                  70                  75                  80

Ser Met Asp Ser Arg Ser Ala Ser His Arg Ser Thr Arg Phe Ala Ala
                85                  90                  95

Thr Phe Tyr Asp Thr Glu Thr Leu Lys Val Ile Asp Glu Glu Trp Gln
            100                 105                 110

Arg Thr Gln Cys Ser Pro Arg Glu Thr Cys Val Glu Val Ala Ser Glu
        115                 120                 125

Leu Gly Lys Thr Thr Asn Thr Phe Phe Lys Pro Pro Cys Val Asn Val
    130                 135                 140

Phe Arg Cys Gly Gly Cys Cys Asn Glu Glu Gly Val Met Cys Met Asn
145                 150                 155                 160
```

```
Thr Ser Thr Ser Tyr Ile Ser Lys Gln Leu Phe Glu Ile Ser Val Pro
                165                 170                 175

Leu Thr Ser Val Pro Glu Leu Val Pro Val Lys Ile Ala Asn His Thr
            180                 185                 190

Gly Cys Lys Cys Leu Pro Thr Gly Pro Arg His Pro Tyr Ser Ile Ile
        195                 200                 205

Arg Arg Ser Ile Gln Thr Pro Glu Glu Asp Glu Cys Pro His Ser Lys
    210                 215                 220

Lys Leu Cys Pro Ile Asp Met Leu Trp Asp Asn Thr Lys Cys Lys Cys
225                 230                 235                 240

Val Leu Gln Asp Glu Thr Pro Leu Pro Gly Thr Glu Asp His Ser Tyr
                245                 250                 255

Leu Gln Glu Pro Thr Leu Cys Gly Pro His Met Thr Phe Asp Glu Asp
            260                 265                 270

Arg Cys Glu Cys Val Cys Lys Ala Pro Cys Pro Gly Asp Leu Ile Gln
        275                 280                 285

His Pro Glu Asn Cys Ser Cys Phe Glu Cys Lys Glu Ser Leu Glu Ser
    290                 295                 300

Cys Cys Gln Lys His Lys Ile Phe His Pro Asp Thr Cys Ser Cys Glu
305                 310                 315                 320

Asp Arg Cys Pro Phe His Thr Arg Thr Cys Ala Ser Arg Lys Pro Ala
                325                 330                 335

Cys Gly Lys His Trp Arg Phe Pro Lys Glu Thr Arg Ala Gln Gly Leu
            340                 345                 350

Tyr Ser Gln Glu Asn Pro
        355

<210> SEQ ID NO 14
<211> LENGTH: 321
<212> TYPE: PRT
<213> ORGANISM: Mus musculus

<400> SEQUENCE: 14

Met Tyr Gly Glu Trp Gly Met Gly Asn Ile Leu Met Met Phe His Val
1               5                   10                  15

Tyr Leu Val Gln Gly Phe Arg Ser Glu His Gly Pro Val Lys Arg Ser
                20                  25                  30

Ser Arg Ser Met Leu Glu Arg Ser Glu Gln Gln Ile Arg Ala Ala Ser
            35                  40                  45

Ser Leu Glu Glu Leu Leu Gln Ile Ala His Ser Glu Asp Trp Lys Leu
        50                  55                  60

Trp Arg Cys Arg Leu Lys Leu Lys Ser Leu Ala Ser Met Asp Ser Arg
65                  70                  75                  80

Ser Ala Ser His Arg Ser Thr Arg Phe Ala Ala Thr Phe Tyr Asp Thr
                85                  90                  95

Glu Thr Leu Lys Val Ile Asp Gly Glu Trp Arg Thr Gln Cys Ser
            100                 105                 110

Pro Arg Glu Thr Cys Val Glu Val Ala Ser Glu Leu Gly Lys Thr Thr
        115                 120                 125

Asn Thr Phe Phe Lys Pro Pro Cys Val Asn Val Phe Arg Cys Gly Gly
    130                 135                 140

Cys Cys Asn Glu Glu Gly Val Met Cys Met Asn Thr Ser Thr Ser Tyr
145                 150                 155                 160

Ile Ser Lys Gln Leu Phe Glu Ile Ser Val Pro Leu Thr Ser Val Pro
                165                 170                 175
```

-continued

```
Glu Leu Val Pro Val Lys Ile Ala Asn His Thr Gly Cys Lys Cys Leu
                180                 185                 190

Pro Thr Gly Pro Arg His Pro Tyr Ser Ile Ile Arg Arg Ser Ile Gln
            195                 200                 205

Thr Pro Glu Glu Asp Glu Cys Pro His Ser Lys Lys Leu Cys Pro Ile
    210                 215                 220

Asp Met Leu Trp Asp Asn Thr Lys Cys Lys Cys Val Leu Gln Asp Glu
225                 230                 235                 240

Thr Pro Leu Pro Gly Thr Glu Asp His Ser Tyr Leu Gln Glu Pro Thr
                245                 250                 255

Leu Cys Gly Pro His Met Thr Phe Asp Glu Asp Arg Cys Glu Cys Val
            260                 265                 270

Cys Lys Ala Pro Cys Pro Gly Asp Leu Ile Gln His Pro Glu Asn Cys
            275                 280                 285

Ser Cys Phe Glu Cys Lys Glu Ser Leu Glu Ser Cys Cys Gln Lys His
    290                 295                 300

Lys Ile Phe His Pro Asp Thr Cys Arg Ser Met Val Phe Ser Leu Ser
305                 310                 315                 320

Pro

<210> SEQ ID NO 15
<211> LENGTH: 109
<212> TYPE: PRT
<213> ORGANISM: Mus musculus

<400> SEQUENCE: 15

Phe Tyr Asp Thr Glu Thr Leu Lys Val Ile Asp Glu Glu Trp Gln Arg
1               5                   10                  15

Thr Gln Cys Ser Pro Arg Glu Thr Cys Val Glu Val Ala Ser Glu Leu
            20                  25                  30

Gly Lys Thr Thr Asn Thr Phe Phe Lys Pro Pro Cys Val Asn Val Phe
        35                  40                  45

Arg Cys Gly Gly Cys Cys Asn Glu Glu Gly Val Met Cys Met Asn Thr
    50                  55                  60

Ser Thr Ser Tyr Ile Ser Lys Gln Leu Phe Glu Ile Ser Val Pro Leu
65                  70                  75                  80

Thr Ser Val Pro Glu Leu Val Pro Val Lys Ile Ala Asn His Thr Gly
                85                  90                  95

Cys Lys Cys Leu Pro Thr Gly Pro Arg His Pro Tyr Ser
            100                 105
```

What is claimed is:

1. A mammalian cell line transformed or transfected with a promoter operably linked to a VEGF-D nucleic acid, wherein the VEGF-D nucleic acid comprises a nucleotide sequence encoding a continuous portion of SEQ ID NO: 11 having a biological activity of VEGF-D selected from the group consisting of ability to stimulate one or more of endothelial cell proliferation, differentiation, migration, survival or vascular permeability,
    wherein the VEGF-D nucleic acid lacks the codons encoding amino acids 203-354 of SEQ ID NO: 11; and
    wherein said promoter is capable of promoting expression of the nucleic acid in a mammalian cell.

2. A mammalian cell line transformed or transfected with a promoter operably linked to a VEGF-D nucleic acid, wherein the VEGF-D nucleic acid comprises a nucleotide sequence encoding a continuous portion of SEQ ID NO: 11 having a biological activity of VEGF-D selected from the group consisting of ability to stimulate one or more of endothelial cell proliferation, differentiation, migration, survival or vascular permeability,
    wherein the VEGF-D nucleic acid lacks the codons encoding amino acids 203-354 of SEQ ID NO: 11, and
    wherein said cell line is the 293-EBNA human embryonal kidney cell line.

3. A mammalian call line transformed or transfected with a promoter operably linked to a VEGF-D nucleic acid, wherein the VEGF-D nucleic acid comprises a nucleotide sequence encoding a continuous portion of SEQ ID NO: 11, wherein the VEGF-D nucleic acid encodes amino acids 2-202 of SEQ ID NO: 11 and wherein the VEGF-D nucleic acid lacks the codons encoding amino acids 203-354 of SEQ ID NO: 11.

4. An expression vector comprising
    a nucleic acid comprising a nucleotide sequence encoding a continuous portion of SEQ ID NO:11 having a biological activity of VEGF-D selected from the group consisting of ability to stimulate one or more of endothelial cell proliferation, differentiation, migration, survival or vascular permeability, wherein the nucleic acid lacks the codons encoding positions 203-354 of SEQ ID NO: 11, and, a promoter operably linked to the nucleic acid, wherein said promoter is capable of promoting expression of the nucleic acid in a mammalian cell.

5. An isolated nucleic acid comprising a nucleotide sequence encoding a continuous portion of SEQ ID NO:11 having a biological activity of VEGF-D selected from the group consisting of ability to stimulate one or more of endothelial cell proliferation, differentiation, migration, survival or vascular permeability, wherein the nucleic acid lacks the codons encoding amino acids 203-354 of SEQ ID NO: 11.

6. The isolated nucleic acid according to claim 5, further comprising sequence that encodes an affinity tag attached in-frame to the nucleotide sequence.

7. An expression vector comprising the nucleic acid according to claim 6.

8. An isolated host cell transformed or transfected with the isolated nucleic acid of claim 5 or the vector according claim 4.

* * * * *

UNITED STATES PATENT AND TRADEMARK OFFICE
CERTIFICATE OF CORRECTION

PATENT NO.         : 7,947,472 B2
APPLICATION NO.    : 09/219345
DATED              : May 24, 2011
INVENTOR(S)        : Marc G. Achen Page 1 of 14

It is certified that error appears in the above-identified patent and that said Letters Patent is hereby corrected as shown below:

In the Specification

At Columns 21-36, the Sequence Listing should be –

```
                      SEQUENCE LISTING

<160> 15

<210> SEQ ID NO 1
   <211> LEGNTH: 109
   <212> TYPE: PRT
   <213> ORGANISM: Homo Sapiens

<400> SEQUENCE: 1

Phe Tyr Asp Ile Glu Thr Leu Lys Val Ile Asp Glu Glu Trp Gln Arg
   1               5                   10                  15

Thr Gln Cys Ser Pro Arg Glu Thr Cys Val Glu Val Ala Ser Glu Leu
               20                  25                  30

Gly Lys Ser Thr Asn Thr Phe Phe Lys Pro Pro Cys Val Asn Val Phe
               35                  40                  45

Arg Cys Gly Gly Cys Cys Asn Glu Glu Ser Leu Ile Cys Met Asn Thr
       50                  55                  60

Ser Thr Ser Tyr Ile Ser Lys Gln Leu Phe Glu Ile Ser Val Pro Leu
   65                  70                  75                  80
```

Signed and Sealed this
Second Day of July, 2013

Teresa Stanek Rea
*Acting Director of the United States Patent and Trademark Office*

```
Thr Ser Val Pro Glu Leu Val Pro Val Lys Val Ala Asn His Thr Gly
                85                  90                  95

Cys Lys Cys Leu Pro Thr Ala Pro Arg His Pro Tyr Ser
                100                 105

<210> SEQ ID NO 2
<211> LEGNTH: 1325
<212> TYPE: PRT
<213> ORGANISM: Homo sapiens
<400> SEQUENCE: 2
Gly Gly Ala Gly Ala Ala Thr Gly Cys Cys Thr Thr Thr Thr Gly Cys
1               5                   10                  15

Ala Ala Cys Ala Cys Thr Thr Thr Cys Ala Gly Thr Ala Gly Cys
                20                  25                  30

Thr Gly Cys Cys Thr Gly Gly Ala Ala Ala Cys Ala Ala Cys Thr Gly
            35                  40                  45

Cys Thr Thr Ala Gly Thr Cys Ala Thr Cys Gly Gly Thr Ala Gly Ala
50                  55                  60

Cys Ala Thr Thr Thr Ala Ala Ala Ala Thr Ala Thr Thr Cys Ala Ala
65                  70                  75                  80

Ala Ala Thr Gly Thr Ala Thr Gly Gly Ala Gly Ala Ala Thr Gly Gly
                85                  90                  95
Gly Gly Ala Ala Thr Gly Gly Gly Ala Ala Thr Ala Thr Cys Cys
                100                 105                 110

Thr Cys Ala Thr Gly Ala Thr Gly Thr Thr Cys Cys Ala Thr Gly Thr
            115                 120                 125

Gly Thr Ala Cys Thr Thr Gly Gly Thr Gly Cys Ala Gly Gly Gly Cys
            130                 135                 140

Thr Thr Cys Ala Gly Gly Ala Gly Cys Gly Ala Ala Cys Ala Thr Gly
145                 150                 155                 160

Gly Ala Cys Cys Ala Gly Thr Gly Ala Ala Gly Gly Ala Thr Thr Thr
                165                 170                 175

Thr Thr Cys Thr Thr Thr Thr Gly Ala Gly Cys Gly Ala Thr Cys Ala
            180                 185                 190

Thr Cys Cys Cys Gly Gly Thr Cys Cys Ala Thr Gly Thr Thr Gly Gly
            195                 200                 205

Ala Ala Cys Gly Ala Thr Cys Thr Gly Ala Ala Cys Ala Ala Cys Ala
            210                 215                 220

Gly Ala Thr Cys Cys Gly Ala Gly Cys Ala Gly Cys Thr Thr Cys Thr
225                 230                 235                 240

Ala Gly Thr Thr Thr Gly Gly Ala Gly Gly Ala Gly Thr Thr Gly Cys
            245                 250                 255

Thr Gly Cys Ala Ala Ala Thr Cys Gly Cys Gly Cys Ala Cys Thr Cys
            260                 265                 270

Thr Gly Ala Gly Gly Ala Cys Thr Gly Gly Ala Ala Gly Cys Thr Gly
            275                 280                 285
```

```
Thr Gly Gly Cys Gly Ala Thr Gly Cys Cys Gly Gly Thr Thr Gly Ala
    290                 295                 300

Ala Gly Cys Thr Cys Ala Ala Ala Gly Thr Cys Thr Thr Gly Cys
305                 310                 315                 320

Cys Ala Gly Thr Ala Thr Gly Gly Ala Cys Thr Cys Ala Cys Gly Cys
                325                 330                 335

Thr Cys Ala Gly Cys Ala Thr Cys Cys Cys Ala Thr Cys Gly Cys Thr
            340                 345                 350

Cys Cys Ala Cys Cys Ala Gly Ala Thr Thr Thr Gly Cys Gly Gly Cys
        355                 360                 365

Ala Ala Cys Thr Thr Thr Cys Thr Ala Thr Gly Ala Cys Ala Cys Thr
    370                 375                 380

Gly Ala Ala Ala Cys Ala Cys Thr Ala Ala Ala Gly Thr Thr Ala
385                 390                 395                 400

Thr Ala Gly Ala Thr Gly Ala Ala Gly Ala Ala Thr Gly Gly Cys Ala
                405                 410                 415

Gly Ala Gly Gly Ala Cys Cys Cys Ala Ala Thr Gly Cys Ala Gly Cys
            420                 425                 430

Cys Cys Thr Ala Gly Ala Gly Ala Gly Ala Cys Ala Thr Gly Cys Gly
        435                 440                 445

Thr Ala Gly Ala Ala Gly Thr Cys Gly Cys Cys Ala Gly Thr Gly Ala
    450                 455                 460

Gly Cys Thr Gly Gly Gly Gly Ala Ala Gly Ala Cys Ala Ala Cys Cys
465                 470                 475                 480

Ala Ala Cys Ala Cys Ala Thr Thr Cys Thr Thr Cys Ala Ala Gly Cys
                485                 490                 495

Cys Cys Cys Cys Cys Thr Gly Thr Gly Thr Ala Ala Ala Thr Gly Thr
            500                 505                 510

Cys Thr Thr Cys Cys Gly Gly Thr Gly Thr Gly Gly Ala Gly Gly Cys
        515                 520                 525

Thr Gly Cys Thr Gly Cys Ala Ala Cys Gly Ala Ala Gly Ala Gly Gly
    530                 535                 540

Gly Thr Gly Thr Gly Ala Thr Gly Thr Gly Thr Ala Thr Gly Ala Ala
545                 550                 555                 560

Cys Ala Cys Ala Ala Gly Cys Ala Cys Cys Thr Cys Cys Thr Ala Cys
                565                 570                 575

Ala Thr Cys Thr Cys Cys Ala Ala Ala Cys Ala Gly Cys Thr Cys Thr
            580                 585                 590

Thr Thr Gly Ala Gly Ala Thr Ala Thr Cys Ala Gly Thr Gly Cys Cys
        595                 600                 605

Thr Cys Thr Gly Ala Cys Ala Thr Cys Ala Gly Thr Gly Cys Cys Cys
    610                 615                 620

Gly Ala Gly Thr Thr Ala Gly Thr Gly Cys Cys Thr Gly Thr Thr Ala
625                 630                 635                 640
```

Ala Ala Ala Thr Thr Gly Cys Cys Ala Ala Cys Cys Ala Thr Ala Cys
            645                 650                 655

Gly Gly Gly Thr Thr Gly Thr Ala Ala Gly Thr Gly Cys Thr Thr Gly
            660                 665                 670

Cys Cys Cys Ala Cys Gly Gly Gly Cys Cys Cys Cys Gly Cys Cys
        675                 680                 685

Ala Thr Cys Cys Thr Thr Ala Cys Thr Cys Ala Ala Thr Thr Ala Thr
    690                 695                 700

Cys Ala Gly Ala Ala Gly Ala Thr Cys Cys Ala Thr Thr Cys Ala Gly
705             710                 715                 720

Ala Cys Cys Cys Cys Ala Gly Ala Ala Gly Ala Ala Gly Ala Thr Gly
            725                 730                 735

Ala Ala Thr Gly Thr Cys Cys Thr Cys Ala Thr Thr Cys Cys Ala Ala
            740                 745                 750

Gly Ala Ala Ala Cys Thr Cys Thr Gly Thr Cys Cys Thr Ala Thr Thr
        755                 760                 765

Gly Ala Cys Ala Thr Gly Cys Thr Gly Thr Gly Gly Gly Ala Thr Ala
    770                 775                 780

Ala Cys Ala Cys Cys Ala Ala Ala Thr Gly Thr Ala Ala Ala Thr Gly
785             790                 795                 800

Thr Gly Thr Thr Thr Thr Gly Cys Ala Ala Gly Ala Cys Gly Ala Gly
            805                 810                 815

Ala Cys Thr Cys Cys Ala Cys Thr Gly Cys Cys Thr Gly Gly Gly Ala
820 825 830

Cys Ala Gly Ala Ala Gly Ala Cys Cys Ala Cys Thr Cys Thr Thr Ala
835 840 845

Cys Cys Thr Cys Cys Ala Gly Gly Ala Ala Cys Cys Cys Ala Cys Thr
850 855 860

Cys Thr Cys Thr Gly Thr Gly Gly Ala Cys Cys Gly Cys Ala Cys Ala
865 870 875 880

Thr Gly Ala Cys Gly Thr Thr Thr Gly Ala Thr Gly Ala Ala Gly Ala
885 890 895

Thr Cys Gly Cys Thr Gly Thr Gly Ala Gly Thr Gly Cys Gly Thr Cys
900 905 910

Thr Gly Thr Ala Ala Ala Gly Cys Ala Cys Cys Ala Thr Gly Thr Cys
915 920 925

Cys Gly Gly Gly Ala Gly Ala Thr Cys Thr Cys Ala Thr Thr Cys Ala
930 935 940

Gly Cys Ala Cys Cys Cys Gly Gly Ala Ala Ala Ala Cys Thr Gly Cys
945 950 955 960

Ala Gly Thr Thr Gly Cys Thr Thr Thr Gly Ala Gly Thr Gly Cys Ala
965 970 975

Ala Ala Gly Ala Ala Ala Gly Thr Cys Thr Gly Gly Ala Gly Ala Gly
980 985 990

```
        Cys Thr Gly Cys Thr Gly Cys Cys  Ala Ala Ala Ala Gly  Cys Ala Cys
                995             1000                  1005

Ala Ala  Gly Ala Thr Thr Thr  Thr Thr Cys Ala Cys   Cys Cys Ala
        1010             1015                 1020

Gly Ala  Cys Ala Cys Cys Thr  Gly Cys Ala Gly Cys   Thr Gly Thr
        1025             1030                 1035

Gly Ala  Gly Gly Ala Cys Ala  Gly Ala Thr Gly Thr   Cys Cys Thr
        1040             1045                 1050

Thr Thr  Thr Cys Ala Cys Ala  Cys Cys Ala Gly Ala   Ala Cys Ala
        1055             1060                 1065

Thr Gly  Thr Gly Cys Ala Ala  Gly Thr Ala Gly Ala   Ala Ala Gly
        1070             1075                 1080

Cys Cys  Ala Gly Cys Cys Thr  Gly Thr Gly Gly Ala   Ala Ala Gly
        1085             1090                 1095

Cys Ala  Cys Thr Gly Gly Cys  Gly Cys Thr Thr Thr   Cys Cys Ala
        1100             1105                 1110

Ala Ala  Gly Gly Ala Gly Ala  Cys Ala Ala Gly Gly   Gly Cys Cys
        1115             1120                 1125

Cys Ala  Gly Gly Gly Ala Cys  Thr Cys Thr Ala Cys   Ala Gly Cys
        1130             1135                 1140

Cys Ala  Gly Gly Ala Gly Ala  Ala Cys Cys Cys Thr   Thr Gly Ala
        1145             1150                 1155

Thr Thr  Cys Ala Ala Cys Thr  Thr Cys Cys Thr Thr   Thr Cys Ala
        1160             1165                 1170

Ala Gly  Thr Cys Cys Cys Cys  Cys Cys Ala Thr Cys   Thr Cys Thr
        1175             1180                 1185

Gly Thr  Cys Ala Thr Thr Thr  Thr Ala Ala Ala Cys   Ala Gly Cys
        1190             1195                 1200

Thr Cys  Ala Cys Thr Gly Cys  Thr Thr Thr Gly Thr   Cys Ala Ala
        1205             1210                 1215

Gly Thr  Thr Gly Cys Thr Gly  Thr Cys Ala Cys Thr   Gly Thr Thr
        1220             1225                 1230

Gly Cys  Cys Cys Ala Cys Thr  Ala Cys Cys Cys Thr   Thr Thr Gly
        1235             1240                 1245

Ala Ala  Cys Ala Thr Gly Thr  Gly Cys Ala Ala Ala   Cys Ala Cys
        1250             1255                 1260

Ala Gly  Ala Cys Ala Cys Ala  Cys Ala Cys Ala Cys   Ala Cys Ala
        1265             1270                 1275

Cys Ala  Cys Ala Cys Ala Cys  Ala Cys Ala Gly Ala   Gly Cys Ala
        1280             1285                 1290

Ala Cys  Thr Ala Gly Gly Ala  Thr Thr Ala Thr Gly   Thr Thr Thr
        1295             1300                 1305

Thr Cys  Thr Ala Gly Gly Thr  Gly Cys Thr Gly Cys   Cys Thr Ala
        1310             1315                 1320

Ala Gly
        1325
```

```
<210> SEQ ID NO 3
<211> LEGNTH: 320
<212> TYPE: PRT
<213> ORGANISM: Homo sapiens
<400> SEQUENCE: 3
Met Tyr Gly Glu Trp Gly Met Gly Asn Ile Leu Met Met Phe His Val
1               5                   10                  15

Tyr Leu Val Gln Gly Phe Arg Ser Glu His Gly Pro Val Lys Arg Ser
            20                  25                  30

Ser Arg Ser Met Leu Glu Arg Ser Glu Gln Gln Ile Arg Ala Ala Ser
        35                  40                  45

Ser Leu Glu Glu Leu Leu Gln Ile Ala His Ser Glu Asp Trp Lys Leu
    50                  55                  60

Trp Arg Cys Arg Leu Lys Leu Lys Ser Leu Ala Ser Met Asp Ser Arg
65                  70                  75                  80

Ser Ala Ser His Arg Ser Thr Arg Phe Ala Ala Thr Phe Tyr Asp Thr
                85                  90                  95

Glu Thr Leu Lys Val Ile Asp Glu Glu Trp Gln Arg Thr Gln Cys Ser
            100                 105                 110

Pro Arg Glu Thr Cys Val Glu Val Ala Ser Glu Leu Gly Lys Thr Thr
        115                 120                 125

Asn Thr Phe Phe Lys Pro Pro Cys Val Asn Val Phe Arg Cys Gly Gly
    130                 135                 140

Cys Cys Asn Glu Glu Gly Val Met Cys Met Asn Thr Ser Thr Ser Tyr
145                 150                 155                 160

Ile Ser Lys Gln Leu Phe Glu Ile Ser Val Pro Leu Thr Ser Val Pro
                165                 170                 175

Glu Leu Val Pro Val Lys Ile Ala Asn His Thr Gly Cys Lys Cys Leu
            180                 185                 190

Pro Thr Gly Pro Arg His Pro Tyr Ser Ile Ile Arg Arg Ser Ile Gln
        195                 200                 205

Thr Pro Glu Glu Asp Glu Cys Pro His Ser Lys Lys Leu Cys Pro Ile
    210                 215                 220

Asp Met Leu Trp Asp Asn Thr Lys Cys Lys Cys Val Leu Gln Asp Glu
225                 230                 235                 240

Thr Pro Leu Pro Gly Thr Glu Asp His Ser Tyr Leu Gln Glu Pro Thr
                245                 250                 255

Leu Cys Gly Pro His Met Thr Phe Asp Glu Asp Arg Cys Glu Cys Val
            260                 265                 270

Cys Lys Ala Pro Cys Pro Gly Asp Leu Ile Gln His Pro Glu Asn Cys
        275                 280                 285

Ser Cys Phe Glu Cys Lys Glu Ser Leu Glu Ser Cys Cys Gln Lys His
    290                 295                 300

Lys Ile Phe His Pro Asp Thr Cys Arg Ser Met Val Phe Ser Leu Ser
305                 310                 315                 320
```

```
<210> SEQ ID NO 4
<211> LEGNTH: 8
<212> TYPE: PRT
<213> ORGANISM: Homo Sapiens
<400> SEQUENCE: 4
Ser Ile Gln Ile Pro Glu Glu Asp
1               5

<210> SEQ ID NO 5
<211> LEGNTH: 9
<212> TYPE: PRT
<213> ORGANISM: Homo Sapiens

<400> SEQUENCE: 5
Arg Ser Ile Gln Ile Pro Glu Glu Asp
1               5

<210> SEQ ID NO 6
<211> LEGNTH: 6
<212> TYPE: PRT
<213> ORGANISM: Homo Sapiens

<400> SEQUENCE: 6
Phe Ala Ala Thr Phe Tyr
1               5

<210> SEQ ID NO 7
<211> LEGNTH: 6
<212> TYPE: PRT
<213> ORGANISM: Homo Sapiens

<400> SEQUENCE: 7
Lys Val Ile Asp Glu Glu
1               5

<210> SEQ ID NO 8
<211> LEGNTH: 7
<212> TYPE: PRT
<213> ORGANISM: Homo Sapiens

<400> SEQUENCE: 8
Arg Phe Ala Ala Thr Phe Tyr
1               5

<210> SEQ ID NO 9
<211> LEGNTH: 7
<212> TYPE: PRT
<213> ORGANISM: Homo Sapiens

<400> SEQUENCE: 9
Leu Lys Val Ile Asp Glu Glu
1               5
```

CERTIFICATE OF CORRECTION (continued)
U.S. Pat. No. 7,947,472 B2

```
<210> SEQ ID NO 10
<211> LEGNTH: 354
<212> TYPE: PRT
<213> ORGANISM: Homo Sapiens
<400> SEQUENCE: 10
Met Tyr Arg Glu Trp Val Val Val Asn Val Phe Met Met Leu Tyr Val
1               5                   10                  15

Gln Leu Val Gln Gly Ser Ser Asn Glu His Gly Pro Val Lys Arg Ser
            20                  25                  30

Ser Gln Ser Thr Leu Glu Arg Ser Glu Gln Gln Ile Arg Ala Ala Ser
        35                  40                  45

Ser Leu Glu Glu Leu Leu Arg Ile Thr His Ser Glu Asp Trp Lys Leu
    50                  55                  60

Trp Arg Cys Arg Leu Arg Leu Lys Ser Phe Thr Ser Met Asp Ser Arg
65                  70                  75                  80

Ser Ala Ser His Arg Ser Thr Arg Phe Ala Ala Thr Phe Tyr Asp Ile
                85                  90                  95

Glu Thr Leu Lys Val Ile Asp Glu Glu Trp Gln Arg Thr Gln Cys Ser
            100                 105                 110

Pro Arg Glu Thr Cys Val Glu Val Ala Ser Glu Leu Gly Lys Ser Thr
        115                 120                 125

Asn Thr Phe Phe Lys Pro Pro Cys Val Asn Val Phe Arg Cys Gly Gly
    130                 135                 140

Cys Cys Asn Glu Glu Ser Leu Ile Cys Met Asn Thr Ser Thr Ser Tyr
145                 150                 155                 160

Ile Ser Lys Gln Leu Phe Glu Ile Ser Val Pro Leu Thr Ser Val Pro
                165                 170                 175

Glu Leu Val Pro Val Lys Val Ala Asn His Thr Gly Cys Lys Cys Leu
            180                 185                 190

Pro Thr Ala Pro Arg His Pro Tyr Ser Ile Ile Arg Arg Ser Ile Gln
        195                 200                 205

Ile Pro Glu Glu Asp Arg Cys Ser His Ser Lys Lys Leu Cys Pro Ile
    210                 215                 220

Asp Met Leu Trp Asp Ser Asn Lys Cys Lys Cys Val Leu Gln Glu Glu
225                 230                 235                 240

Asn Pro Leu Ala Gly Thr Glu Asp His Ser His Leu Gln Glu Pro Ala
                245                 250                 255

Leu Cys Gly Pro His Met Met Phe Asp Glu Asp Arg Cys Glu Cys Val
            260                 265                 270

Cys Lys Thr Pro Cys Pro Lys Asp Leu Ile Gln His Pro Lys Asn Cys
        275                 280                 285

Ser Cys Phe Glu Cys Lys Glu Ser Leu Glu Thr Cys Cys Gln Lys His
    290                 295                 300

Lys Leu Phe His Pro Asp Thr Cys Ser Cys Glu Asp Arg Cys Pro Phe
305                 310                 315                 320
```

```
His Thr Arg Pro Cys Ala Ser Gly Lys Thr Ala Cys Ala Lys His Cys
                325                 330                 335

Arg Phe Pro Lys Glu Lys Arg Ala Ala Gln Gly Pro His Ser Arg Lys
            340                 345                 350

Asn Pro

<210> SEQ ID NO 11
<211> LEGNTH: 354
<212> TYPE: PRT
<213> ORGANISM: Homo Sapiens
<400> SEQUENCE: 11
Met Tyr Arg Glu Trp Val Val Asn Val Phe Met Met Leu Tyr Val
1               5                   10                  15

Gln Leu Val Gln Gly Ser Ser Asn Glu His Gly Pro Val Lys Arg Ser
            20                  25                  30

Ser Gln Ser Thr Leu Glu Arg Ser Glu Gln Gln Ile Arg Ala Ala Ser
        35                  40                  45

Ser Leu Glu Glu Leu Leu Arg Ile Thr His Ser Glu Asp Trp Lys Leu
    50                  55                  60

Trp Arg Cys Arg Leu Arg Leu Lys Ser Phe Thr Ser Met Asp Ser Arg
65                  70                  75                  80

Ser Ala Ser His Arg Ser Thr Arg Phe Ala Ala Thr Phe Tyr Asp Ile
                85                  90                  95

Glu Thr Leu Lys Val Ile Asp Glu Glu Trp Gln Arg Thr Gln Cys Ser
            100                 105                 110

Pro Arg Glu Thr Cys Val Glu Val Ala Ser Glu Leu Gly Lys Ser Thr
            115                 120                 125

Asn Thr Phe Phe Lys Pro Pro Cys Val Asn Val Phe Arg Cys Gly Gly
        130                 135                 140

Cys Cys Asn Glu Glu Ser Leu Ile Cys Met Asn Thr Ser Thr Ser Tyr
145                 150                 155                 160

Ile Ser Lys Gln Leu Phe Glu Ile Ser Val Pro Leu Thr Ser Val Pro
                165                 170                 175

Glu Leu Val Pro Val Lys Val Ala Asn His Thr Gly Cys Lys Cys Leu
            180                 185                 190

Pro Thr Ala Pro Arg His Pro Tyr Ser Ile Ile Arg Arg Ser Ile Gln
            195                 200                 205

Ile Pro Glu Glu Asp Arg Cys Ser His Ser Lys Lys Leu Cys Pro Ile
        210                 215                 220
```

```
Asp Met Leu Trp Asp Ser Asn Lys Cys Lys Cys Val Leu Gln Glu Glu
225                 230                 235                 240

Asn Pro Leu Ala Gly Thr Glu Asp His Ser His Leu Gln Glu Pro Ala
                245                 250                 255

Leu Cys Gly Pro His Met Met Phe Asp Glu Asp Arg Cys Glu Cys Val
            260                 265                 270

Cys Lys Thr Pro Cys Pro Lys Asp Leu Ile Gln His Pro Lys Asn Cys
        275                 280                 285

Ser Cys Phe Glu Cys Lys Glu Ser Leu Glu Thr Cys Cys Gln Lys His
    290                 295                 300

Lys Leu Phe His Pro Asp Thr Cys Ser Cys Glu Asp Arg Cys Pro Phe
305                 310                 315                 320

His Thr Arg Pro Cys Ala Ser Gly Lys Thr Ala Cys Ala Lys His Cys
                325                 330                 335

Arg Phe Pro Lys Glu Lys Arg Ala Ala Gln Gly Pro His Ser Arg Lys
            340                 345                 350

Asn Pro

<210> SEQ ID NO 12
<211> LEGNTH: 325
<212> TYPE: PRT
<213> ORGANISM: Homo sapiens

<400> SEQUENCE: 12

Met Arg Ser Ser Gln Ser Thr Leu Glu Arg Ser Glu Gln Gln Ile Arg
1               5                   10                  15

Ala Ala Ser Ser Leu Glu Glu Leu Leu Arg Ile Thr His Ser Glu Asp
                20                  25                  30

Trp Lys Leu Trp Arg Cys Arg Leu Arg Leu Lys Ser Phe Thr Ser Met
            35                  40                  45

Asp Ser Arg Ser Ala Ser His Arg Ser Thr Arg Phe Ala Ala Thr Phe
        50                  55                  60

Tyr Asp Ile Glu Thr Leu Lys Val Ile Asp Glu Glu Trp Gln Arg Thr
65                  70                  75                  80

Gln Cys Ser Pro Arg Glu Thr Cys Val Glu Val Ala Ser Glu Leu Gly
                85                  90                  95

Lys Ser Thr Asn Thr Phe Phe Lys Pro Pro Cys Val Asn Val Phe Arg
                100                 105                 110

Cys Gly Gly Cys Cys Asn Glu Glu Ser Leu Ile Cys Met Asn Thr Ser
            115                 120                 125

Thr Ser Tyr Ile Ser Lys Gln Leu Phe Glu Ile Ser Val Pro Leu Thr
        130                 135                 140
```

```
Ser Val Pro Glu Leu Val Pro Val Lys Val Ala Asn His Thr Gly Cys
145                 150                 155                 160

Lys Cys Leu Pro Thr Ala Pro Arg His Pro Tyr Ser Ile Ile Arg Arg
                165                 170                 175

Ser Ile Gln Ile Pro Glu Glu Asp Arg Cys Ser His Ser Lys Lys Leu
                180                 185                 190

Cys Pro Ile Asp Met Leu Trp Asp Ser Asn Lys Cys Lys Cys Val Leu
            195                 200                 205

Gln Glu Glu Asn Pro Leu Ala Gly Thr Glu Asp His Ser His Leu Gln
        210                 215                 220

Glu Pro Ala Leu Cys Gly Pro His Met Met Phe Asp Glu Asp Arg Cys
225                 230                 235                 240

Glu Cys Val Cys Lys Thr Pro Cys Pro Lys Asp Leu Ile Gln His Pro
                245                 250                 255

Lys Asn Cys Ser Cys Phe Glu Cys Lys Glu Ser Leu Glu Thr Cys Cys
                260                 265                 270

Gln Lys His Lys Leu Phe His Pro Asp Thr Cys Ser Cys Glu Asp Arg
            275                 280                 285

Cys Pro Phe His Thr Arg Pro Cys Ala Ser Gly Lys Thr Ala Cys Ala
        290                 295                 300

Lys His Cys Arg Phe Pro Lys Glu Lys Arg Ala Ala Gln Gly Pro His
305                 310                 315                 320

Ser Arg Lys Asn Pro
                325

<210> SEQ ID NO 13
<211> LEGNTH: 358
<212> TYPE: PRT
<213> ORGANISM: Mus musculus

<400> SEQUENCE: 13

Met Tyr Gly Glu Trp Gly Met Gly Asn Ile Leu Met Met Phe His Val
1               5                   10                  15

Tyr Leu Val Gln Gly Phe Arg Ser Glu His Gly Pro Val Lys Asp Phe
                20                  25                  30

Ser Phe Glu Arg Ser Ser Arg Ser Met Leu Glu Arg Ser Glu Gln Gln
            35                  40                  45

Ile Arg Ala Ala Ser Ser Leu Glu Glu Leu Leu Gln Ile Ala His Ser
        50                  55                  60

Glu Asp Trp Lys Leu Trp Arg Cys Arg Leu Lys Leu Lys Ser Leu Ala
65                  70                  75                  80

Ser Met Asp Ser Arg Ser Ala Ser His Arg Ser Thr Arg Phe Ala Ala
                85                  90                  95

Thr Phe Tyr Asp Thr Glu Thr Leu Lys Val Ile Asp Glu Glu Trp Gln
                100                 105                 110

Arg Thr Gln Cys Ser Pro Arg Glu Thr Cys Val Glu Val Ala Ser Glu
            115                 120                 125

Leu Gly Lys Thr Thr Asn Thr Phe Phe Lys Pro Pro Cys Val Asn Val
        130                 135                 140
```

```
Phe Arg Cys Gly Gly Cys Cys Asn Glu Glu Gly Val Met Cys Met Asn
145                 150                 155                 160

Thr Ser Thr Ser Tyr Ile Ser Lys Gln Leu Phe Glu Ile Ser Val Pro
            165                 170                 175

Leu Thr Ser Val Pro Glu Leu Val Pro Val Lys Ile Ala Asn His Thr
            180                 185                 190

Gly Cys Lys Cys Leu Pro Thr Gly Pro Arg His Pro Tyr Ser Ile Ile
            195                 200                 205

Arg Arg Ser Ile Gln Thr Pro Glu Glu Asp Glu Cys Pro His Ser Lys
210                 215                 220

Lys Leu Cys Pro Ile Asp Met Leu Trp Asp Asn Thr Lys Cys Lys Cys
225                 230                 235                 240

Val Leu Gln Asp Glu Thr Pro Leu Pro Gly Thr Glu Asp His Ser Tyr
            245                 250                 255

Leu Gln Glu Pro Thr Leu Cys Gly Pro His Met Thr Phe Asp Glu Asp
            260                 265                 270

Arg Cys Glu Cys Val Cys Lys Ala Pro Cys Pro Gly Asp Leu Ile Gln
            275                 280                 285

His Pro Glu Asn Cys Ser Cys Phe Glu Cys Lys Glu Ser Leu Glu Ser
        290                 295                 300

Cys Cys Gln Lys His Lys Ile Phe His Pro Asp Thr Cys Ser Cys Glu
305                 310                 315                 320

Asp Arg Cys Pro Phe His Thr Arg Thr Cys Ala Ser Arg Lys Pro Ala
                325                 330                 335

Cys Gly Lys His Trp Arg Phe Pro Lys Glu Thr Arg Ala Gln Gly Leu
            340                 345                 350

Tyr Ser Gln Glu Asn Pro
        355

<210> SEQ ID NO 14
<211> LEGNTH: 321
<212> TYPE: PRT
<213> ORGANISM: Mus musculus

<400> SEQUENCE: 14

Met Tyr Gly Glu Trp Gly Met Gly Asn Ile Leu Met Met Phe His Val
1               5                   10                  15

Tyr Leu Val Gln Gly Phe Arg Ser Glu His Gly Pro Val Lys Arg Ser
            20                  25                  30
Ser Arg Ser Met Leu Glu Arg Ser Glu Gln Gln Ile Arg Ala Ala Ser
            35                  40                  45

Ser Leu Glu Glu Leu Leu Gln Ile Ala His Ser Glu Asp Trp Lys Leu
        50                  55                  60

Trp Arg Cys Arg Leu Lys Leu Lys Ser Leu Ala Ser Met Asp Ser Arg
65                  70                  75                  80

Ser Ala Ser His Arg Ser Thr Arg Phe Ala Ala Thr Phe Tyr Asp Thr
            85                  90                  95
```

```
       Glu Thr Leu Lys Val Ile Asp Glu Glu Trp Gln Arg Thr Gln Cys Ser
                   100                 105                 110

Pro Arg Glu Thr Cys Val Glu Val Ala Ser Glu Leu Gly Lys Thr Thr
                   115                 120                 125

Asn Thr Phe Phe Lys Pro Pro Cys Val Asn Val Phe Arg Cys Gly Gly
                   130                 135                 140

Cys Cys Asn Glu Glu Gly Val Met Cys Met Asn Thr Ser Thr Ser Tyr
       145                 150                 155                 160

Ile Ser Lys Gln Leu Phe Glu Ile Ser Val Pro Leu Thr Ser Val Pro
                   165                 170                 175

Glu Leu Val Pro Val Lys Ile Ala Asn His Thr Gly Cys Lys Cys Leu
                   180                 185                 190

Pro Thr Gly Pro Arg His Pro Tyr Ser Ile Ile Arg Arg Ser Ile Gln
                   195                 200                 205

Thr Pro Glu Glu Asp Glu Cys Pro His Ser Lys Lys Leu Cys Pro Ile
                   210                 215                 220

Asp Met Leu Trp Asp Asn Thr Lys Cys Lys Cys Val Leu Gln Asp Glu
       225                 230                 235                 240

Thr Pro Leu Pro Gly Thr Glu Asp His Ser Tyr Leu Gln Glu Pro Thr
                   245                 250                 255

Leu Cys Gly Pro His Met Thr Phe Asp Glu Asp Arg Cys Glu Cys Val
                   260                 265                 270

Cys Lys Ala Pro Cys Pro Gly Asp Leu Ile Gln His Pro Glu Asn Cys
                   275                 280                 285

Ser Cys Phe Glu Cys Lys Glu Ser Leu Glu Ser Cys Cys Gln Lys His
                   290                 295                 300

Lys Ile Phe His Pro Asp Thr Cys Arg Ser Met Val Phe Ser Leu Ser
       305                 310                 315                 320

Pro

<210> SEQ ID NO 15
       <211> LEGNTH: 109
       <212> TYPE: PRT
       <213> ORGANISM: Mus musculus

<400> SEQUENCE: 15

Phe Tyr Asp Thr Glu Thr Leu Lys Val Ile Asp Glu Glu Trp Gln Arg
       1               5                   10                  15

Thr Gln Cys Ser Pro Arg Glu Thr Cys Val Glu Val Ala Ser Glu Leu
                   20                  25                  30

Gly Lys Thr Thr Asn Thr Phe Phe Lys Pro Pro Cys Val Asn Val Phe
                   35                  40                  45

Arg Cys Gly Gly Cys Cys Asn Glu Glu Gly Val Met Cys Met Asn Thr
                   50                  55                  60

Ser Thr Ser Tyr Ile Ser Lys Gln Leu Phe Glu Ile Ser Val Pro Leu
       65                  70                  75                  80
```

CERTIFICATE OF CORRECTION (continued)
U.S. Pat. No. 7,947,472 B2

```
Thr Ser Val Pro Glu Leu Val Pro Val Lys Ile Ala Asn His Thr Gly
            85                  90                  95

Cys Lys Cys Leu Pro Thr Gly Pro Arg His Pro Tyr Ser
            100             105
```